(12) United States Patent
Sklar

(10) Patent No.: US 12,345,373 B2
(45) Date of Patent: Jul. 1, 2025

(54) BASE STATION ASSEMBLY FOR AN OPERATING ROOM TABLE

(71) Applicant: Frederick H. Sklar, Dallas, TX (US)

(72) Inventor: Frederick H. Sklar, Dallas, TX (US)

( * ) Notice: Subject to any disclaimer, the term of this patent is extended or adjusted under 35 U.S.C. 154(b) by 0 days.

(21) Appl. No.: 18/502,825

(22) Filed: Nov. 6, 2023

(65) Prior Publication Data

US 2024/0148587 A1    May 9, 2024

Related U.S. Application Data

(60) Provisional application No. 63/382,685, filed on Nov. 7, 2022.

(51) Int. Cl.
| | |
|---|---|
| *F16M 11/42* | (2006.01) |
| *A61B 90/57* | (2016.01) |
| *A61G 13/12* | (2006.01) |
| *F16M 11/04* | (2006.01) |

(52) U.S. Cl.
CPC ...... *F16M 11/425* (2013.01); *A61B 2090/571* (2016.02); *A61G 13/121* (2013.01); *F16M 11/046* (2013.01); *F16M 2200/021* (2013.01); *F16M 2200/022* (2013.01); *F16M 2200/025* (2013.01); *F16M 2200/08* (2013.01)

(58) Field of Classification Search
CPC ........... F16M 11/425; F16M 2200/025; F16M 2200/027; A61B 2090/571; A61B 90/57; F16B 2/06; F16B 2/12; F16B 2/16
USPC ...................................................... 248/187.1
See application file for complete search history.

(56) References Cited

U.S. PATENT DOCUMENTS

| | | | |
|---|---|---|---|
| 2,494,792 | A | 1/1950 | Bloom |
| 2,709,070 | A | 5/1955 | Bielstein |
| 2,966,383 | A | 12/1960 | Boetcker et al. |
| 3,072,118 | A | 1/1963 | Standerwick et al. |
| 3,099,441 | A | 7/1963 | Ries |

(Continued)

FOREIGN PATENT DOCUMENTS

| | | |
|---|---|---|
| EP | 2316521 | 5/2011 |
| JP | S55-052747 | 4/1980 |

(Continued)

OTHER PUBLICATIONS

International Search Report and Written Opinion dated Mar. 1, 2011 regarding Intl. Patent Application No. PCT/US2011/020906; 9 pgs.

(Continued)

*Primary Examiner* — Christopher Garft
(74) *Attorney, Agent, or Firm* — Scott Griggs; Griggs Bergen LLP

(57) ABSTRACT

A base station assembly for an operating room table is disclosed. In one embodiment, the base station assembly includes a base station that is secured to the operating room table. The base station includes an arcuate rail member with a selectively moveable clamp attached thereto. A vertical support arm extends from the selectively moveable clamp to provide selective attachment to a surgical accessory, such as a retractor arm, armrest, or image guidance reference frame. The base station assembly provides surgical accessory support that may be moved and adjusted by a surgeon at any time during an operation without contaminating a surgical field and without assistance from circulating operating room personnel.

10 Claims, 16 Drawing Sheets

(56) References Cited

U.S. PATENT DOCUMENTS

| | | | |
|---|---|---|---|
| 3,168,274 A | 2/1965 | Street | |
| 3,522,799 A | 8/1970 | Gauthier | |
| 3,604,412 A | 9/1971 | Gardner | |
| 3,699,799 A | 10/1972 | Hespenhide | |
| 3,810,462 A | 5/1974 | Szpur | |
| 3,835,861 A | 9/1974 | Kees, Jr. et al. | |
| 3,923,046 A | 12/1975 | Heifetz | |
| 3,958,558 A | 5/1976 | Dunphy et al. | |
| 4,014,319 A | 3/1977 | Favre | |
| 4,108,426 A | 8/1978 | Lindstroem et al. | |
| 4,143,652 A * | 3/1979 | Meier | A61B 90/50 600/230 |
| 4,169,478 A | 10/1979 | Hickmann | |
| 4,254,763 A | 3/1981 | Cready et al. | |
| 4,281,667 A | 8/1981 | Cosman | |
| 4,360,028 A | 11/1982 | Moran et al. | |
| 4,444,179 A | 4/1984 | Trippi | |
| 4,457,300 A | 7/1984 | Budde | |
| 4,465,069 A | 8/1984 | Moran et al. | |
| 4,545,572 A | 10/1985 | Day | |
| 4,667,660 A | 5/1987 | Eingorn | |
| 4,681,559 A | 7/1987 | Hooven | |
| 4,700,691 A | 10/1987 | Tari et al. | |
| 4,995,401 A | 2/1991 | Bunegin et al. | |
| 5,147,287 A | 9/1992 | Jewell et al. | |
| 5,197,965 A | 3/1993 | Cherry et al. | |
| 5,205,815 A | 4/1993 | Saunders | |
| 5,214,815 A | 6/1993 | Agbodoe et al. | |
| 5,254,079 A | 10/1993 | Agbodoe et al. | |
| 5,269,034 A | 12/1993 | Day et al. | |
| 5,276,927 A | 1/1994 | Day | |
| 5,284,129 A | 2/1994 | Agbodoe et al. | |
| 5,284,130 A | 2/1994 | Ratliff | |
| 5,317,771 A | 6/1994 | Cook | |
| 5,318,509 A | 6/1994 | Agbodoe | |
| 5,326,374 A | 7/1994 | Ilbawi et al. | |
| 5,347,894 A | 9/1994 | Fischer | |
| 5,400,772 A * | 3/1995 | LeVahn | A61B 17/02 5/503.1 |
| 5,476,241 A * | 12/1995 | Helman | F16M 11/24 248/286.1 |
| 5,529,358 A | 6/1996 | Dinkler et al. | |
| 5,537,704 A | 7/1996 | Dinkler | |
| 5,564,663 A | 10/1996 | Cook et al. | |
| 5,674,186 A | 10/1997 | Guigui et al. | |
| D389,242 S | 1/1998 | Boookwaler et al. | |
| 5,806,512 A | 9/1998 | Abramov et al. | |
| 5,832,926 A | 11/1998 | Towlen | |
| 5,984,864 A | 11/1999 | Fox et al. | |
| 6,117,143 A | 9/2000 | Hynes et al. | |
| 6,179,846 B1 | 1/2001 | McFadden | |
| 6,283,934 B1 | 9/2001 | Borgesen | |
| 6,306,085 B1 | 10/2001 | Farascioni | |
| 6,306,146 B1 | 10/2001 | Dinkler | |
| 6,315,783 B1 | 11/2001 | Katz et al. | |
| 6,368,330 B1 | 4/2002 | Hynes et al. | |
| 6,381,783 B2 | 5/2002 | Reinhardt et al. | |
| 6,416,468 B2 | 7/2002 | Deckman et al. | |
| 6,463,765 B2 | 10/2002 | Blakely | |
| 6,557,195 B2 | 5/2003 | Dinkler | |
| 6,584,630 B1 | 7/2003 | Dinkler | |
| 6,594,839 B1 | 7/2003 | Papay | |
| 6,602,190 B2 | 8/2003 | Dobrovolny | |
| 6,629,982 B2 | 10/2003 | Day et al. | |
| 6,684,428 B2 | 2/2004 | Grotehuis et al. | |
| 6,698,044 B2 | 3/2004 | Greenfield et al. | |
| 6,770,082 B2 | 8/2004 | Dominguez et al. | |
| 7,024,892 B2 | 4/2006 | Blakely | |
| 7,117,551 B1 | 10/2006 | Dinkler, II et al. | |
| 7,229,451 B2 | 6/2007 | Day et al. | |
| 7,232,411 B2 | 6/2007 | Dinkler, II et al. | |
| 7,326,177 B2 | 2/2008 | Williamson, IV et al. | |
| 7,507,244 B2 | 3/2009 | Dinkler | |
| 7,510,533 B2 | 3/2009 | Mauge et al. | |
| 7,552,492 B2 | 6/2009 | Rolfes et al. | |
| 7,730,563 B1 | 6/2010 | Sklar et al. | |
| 7,882,574 B2 | 2/2011 | Arsenault | |
| 7,945,970 B2 | 5/2011 | Belluye et al. | |
| 7,949,394 B2 | 5/2011 | Salo et al. | |
| 8,037,884 B2 | 10/2011 | Weinstein et al. | |
| 8,105,256 B1 | 1/2012 | Ariza | |
| 8,257,289 B2 | 9/2012 | Vess | |
| 8,292,856 B2 | 10/2012 | Bertrand et al. | |
| 8,568,195 B1 | 10/2013 | Schindler | |
| 8,646,452 B2 | 2/2014 | Sklar | |
| 8,801,711 B2 | 8/2014 | Solomon et al. | |
| 8,833,707 B2 * | 9/2014 | Steinberg | A61G 13/102 248/101 |
| 9,033,909 B2 | 5/2015 | Aihara | |
| 9,211,224 B2 | 12/2015 | Sklar | |
| 9,216,125 B2 | 12/2015 | Sklar | |
| 9,717,890 B2 | 8/2017 | Holper et al. | |
| 9,925,360 B2 | 3/2018 | Ludin et al. | |
| 10,743,954 B2 | 8/2020 | Sklar | |
| 11,103,683 B1 | 8/2021 | Sklar | |
| 11,154,695 B2 | 10/2021 | Sklar | |
| 11,324,933 B2 | 5/2022 | Sklar | |
| 11,389,630 B2 | 7/2022 | Sklar | |
| 11,471,231 B2 | 10/2022 | Sklar et al. | |
| 11,678,947 B2 | 6/2023 | Sklar | |
| 2001/0029379 A1 | 10/2001 | Grotehuis et al. | |
| 2002/0042619 A1 | 4/2002 | Dominguez et al. | |
| 2002/0151907 A1 | 10/2002 | Day et al. | |
| 2004/0097985 A1 | 5/2004 | Day et al. | |
| 2005/0075650 A1 | 4/2005 | Dinkler | |
| 2005/0277832 A1 | 12/2005 | Foley et al. | |
| 2006/0076464 A1 * | 4/2006 | Van | F16M 11/18 248/122.1 |
| 2006/0255220 A1 * | 11/2006 | Skripps | A61G 13/04 248/228.4 |
| 2008/0139959 A1 | 6/2008 | Miethke et al. | |
| 2008/0269777 A1 | 10/2008 | Appenrodt et al. | |
| 2009/0138064 A1 | 5/2009 | Horn | |
| 2009/0192432 A1 | 7/2009 | Frazer | |
| 2009/0204019 A1 | 8/2009 | Ginggen et al. | |
| 2009/0254017 A1 | 10/2009 | Dumpson et al. | |
| 2009/0287084 A1 | 11/2009 | Ragauskas et al. | |
| 2009/0299258 A1 | 12/2009 | Cureington-Sims | |
| 2010/0117281 A1 * | 5/2010 | Doyle | F16B 2/185 269/254 R |
| 2011/0054373 A1 | 3/2011 | Reiley | |
| 2011/0066072 A1 | 3/2011 | Kawoos et al. | |
| 2011/0168184 A1 | 7/2011 | Sklar | |
| 2012/0226215 A1 | 9/2012 | Hsu et al. | |
| 2013/0085400 A1 | 4/2013 | Oliveira et al. | |
| 2013/0095730 A1 | 4/2013 | Jensen | |
| 2014/0378774 A1 | 12/2014 | Wooster | |
| 2015/0005800 A1 | 1/2015 | Anite | |
| 2015/0268673 A1 | 9/2015 | Farzbod et al. | |
| 2019/0009014 A1 | 1/2019 | Chen et al. | |
| 2020/0061355 A1 | 2/2020 | Barnea et al. | |
| 2022/0257913 A1 | 8/2022 | Sklar | |

FOREIGN PATENT DOCUMENTS

| | | |
|---|---|---|
| JP | H09-075369 | 3/1997 |
| JP | H09-147142 | 6/1997 |
| WO | 2018227022 | 12/2018 |
| WO | 2019241753 | 12/2019 |

OTHER PUBLICATIONS

International Search Report and Written Opinion dated Oct. 18, 2012 regarding Intl. Patent Application No. PCT/US12/47894; 11 pgs.

International Search Report and Written Opinion dated May 6, 2013 regarding Intl. Patent Application No. PCT/US13/26207; 16 pgs.

International Search Report and Written Opinion dated Jun. 30, 2021 regarding Intl. Patent Application No. PCT/US21/17365; 12 pgs.

(56) References Cited

OTHER PUBLICATIONS

Turnbull et al.; "Post-dural puncture headache: pathogenesis, prevention and treatment"; British Journal of Anaesthesia; 2003; 91(5); pp. 718-729.
International Search Report and Written Opinion dated Aug. 31, 2018 regarding Intl. Patent Application No. PCT/US18/36558; 12 pgs.
Farlex Partner Medical Dictionary. S.v. "costal marin." Retrieved Jan. 11, 2016 from http://medical-dictionary.thefreedictionary.com/costal+margin; 1 pg.
Sklar et al.; "The Use of Abdominal Binders to Treat Over-Shunting Headaches"; J. Neurosurg. Pediatr.; Jun. 2012; 9 (6); pp. 615-620; doI: 10.3171/2012.2.PEDS11146; Children's Medical Center, Dallas, Texas, USA.

* cited by examiner

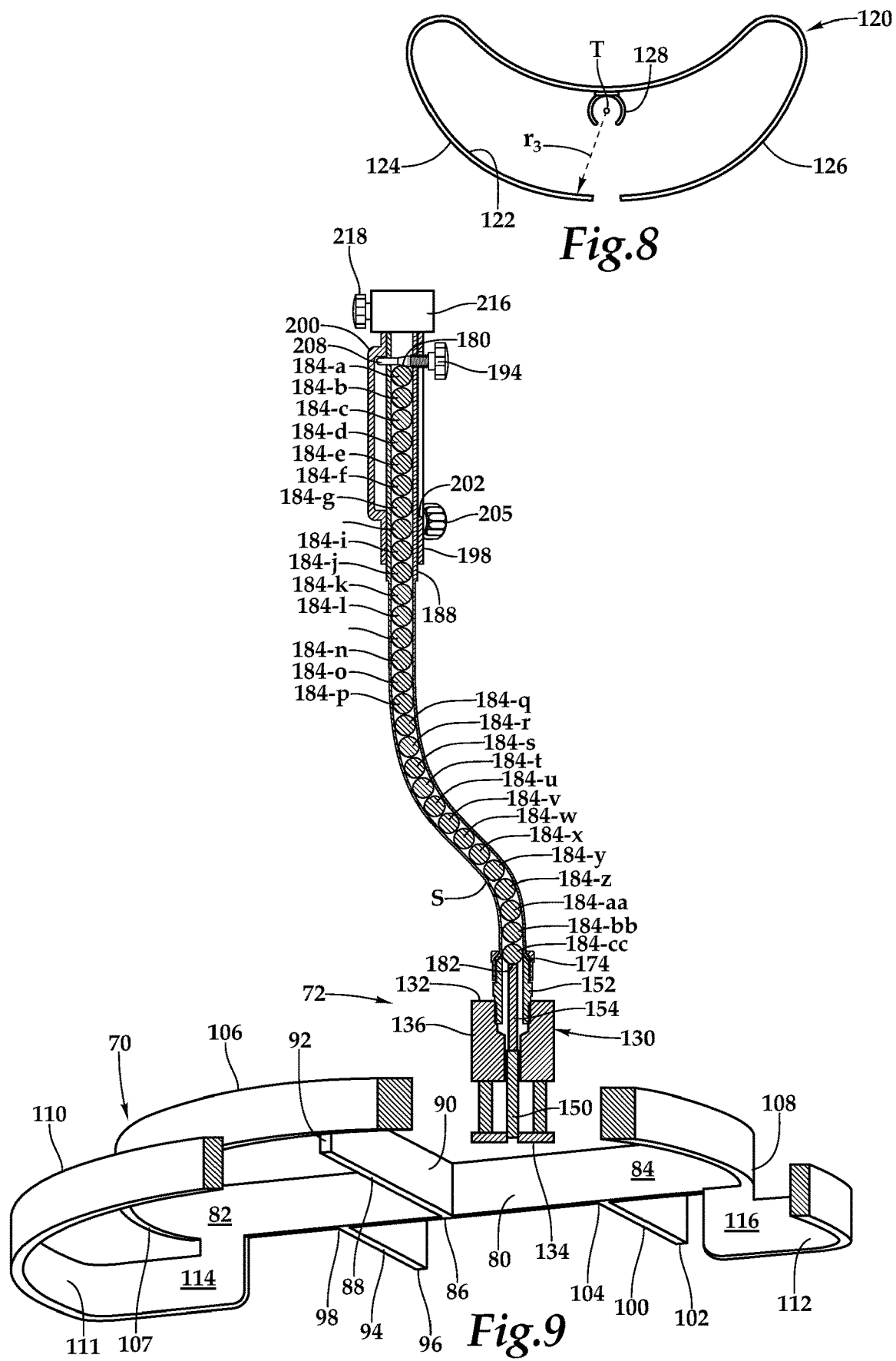

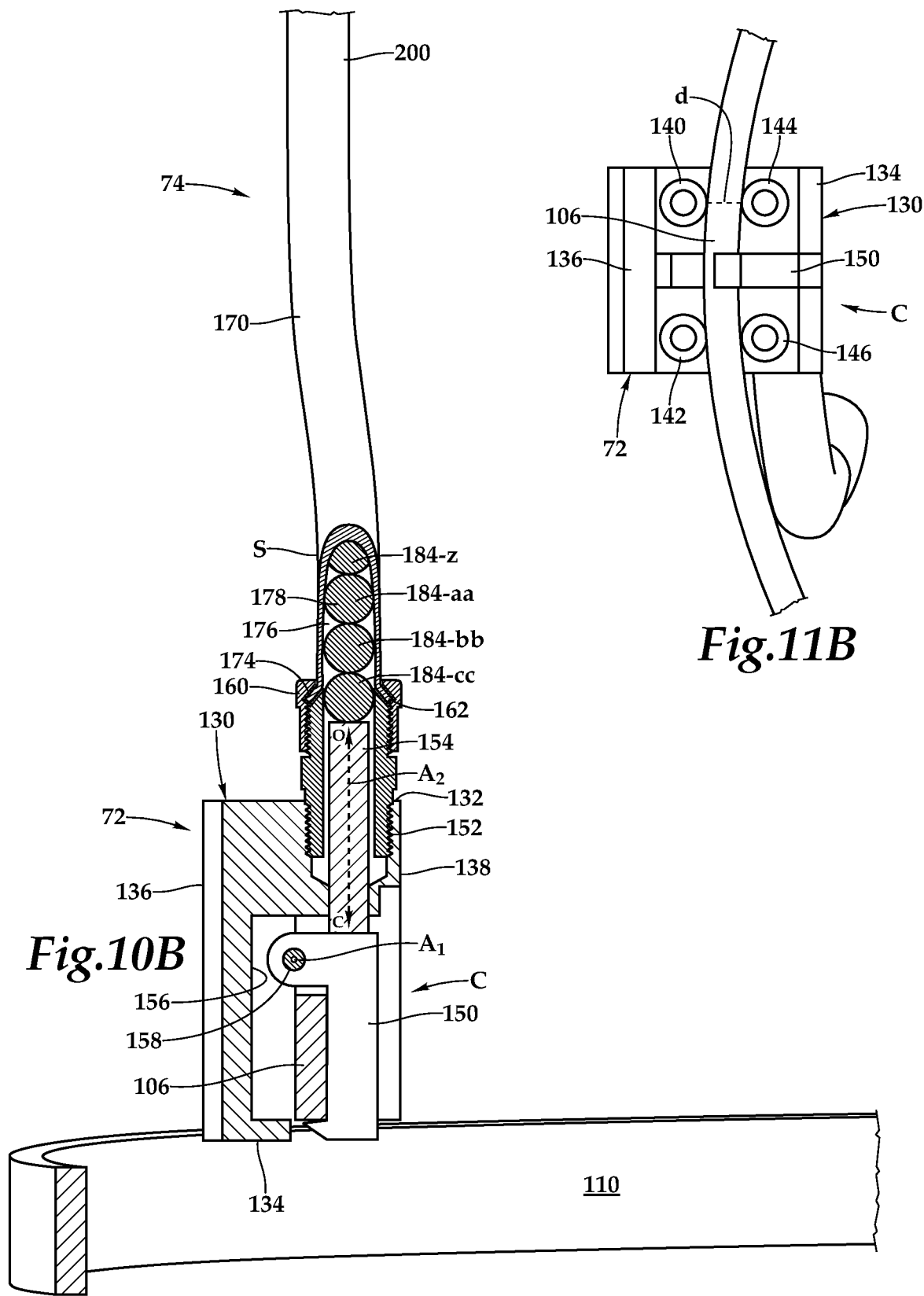

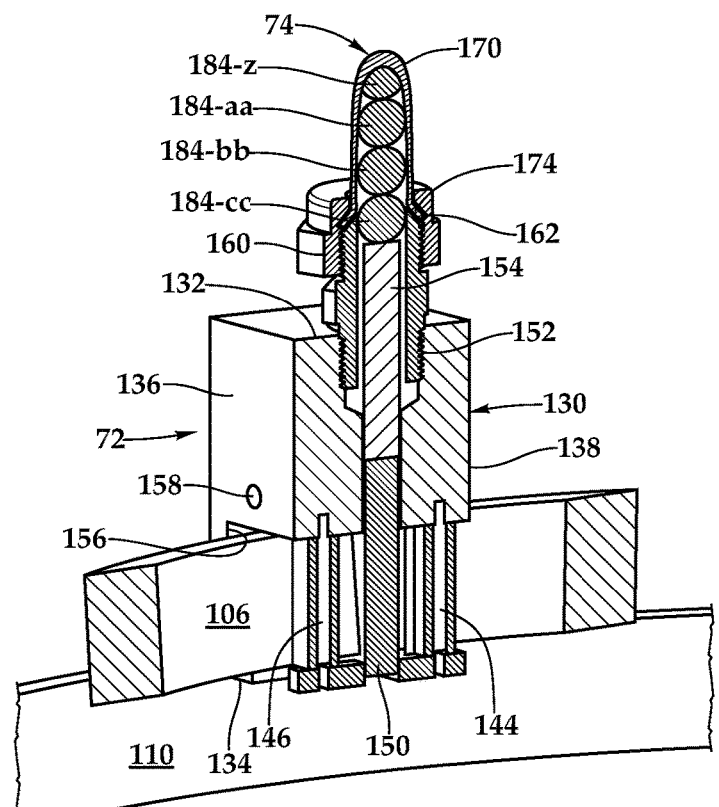
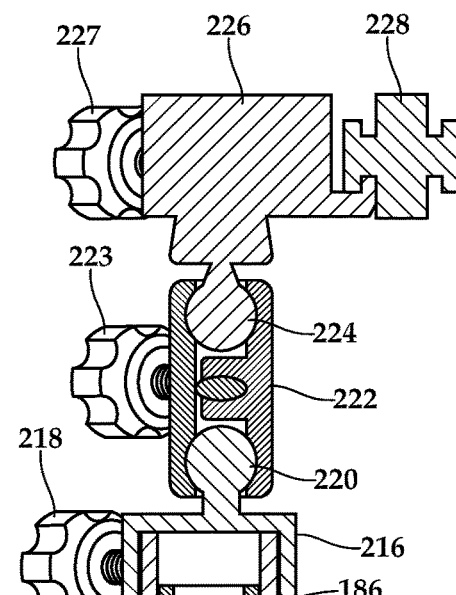
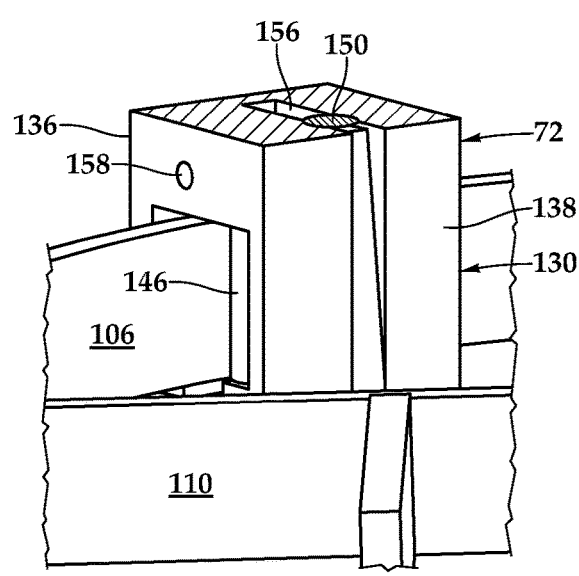
Fig.12
Fig.13
Fig.14

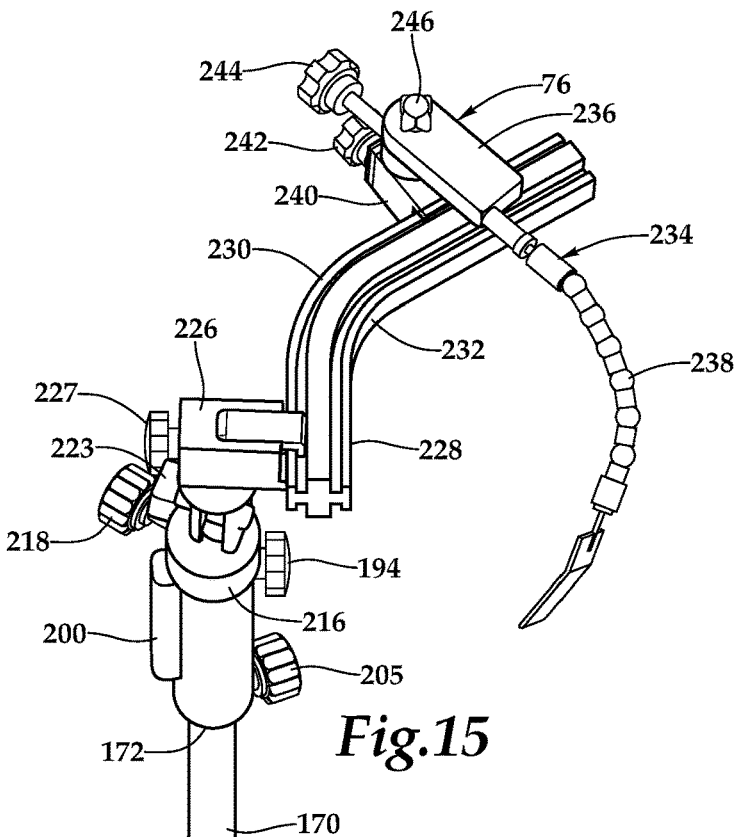
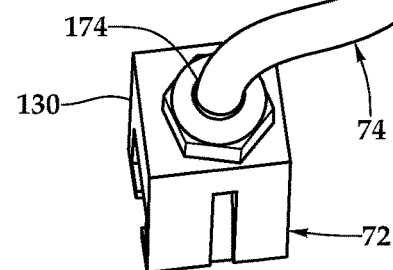
Fig.15
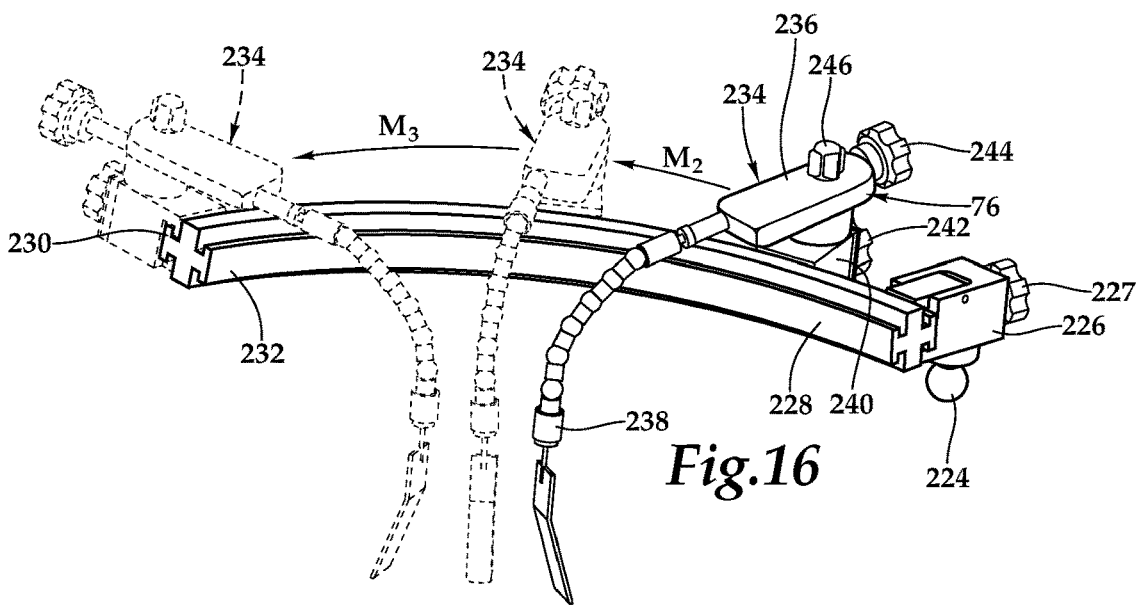
Fig.16

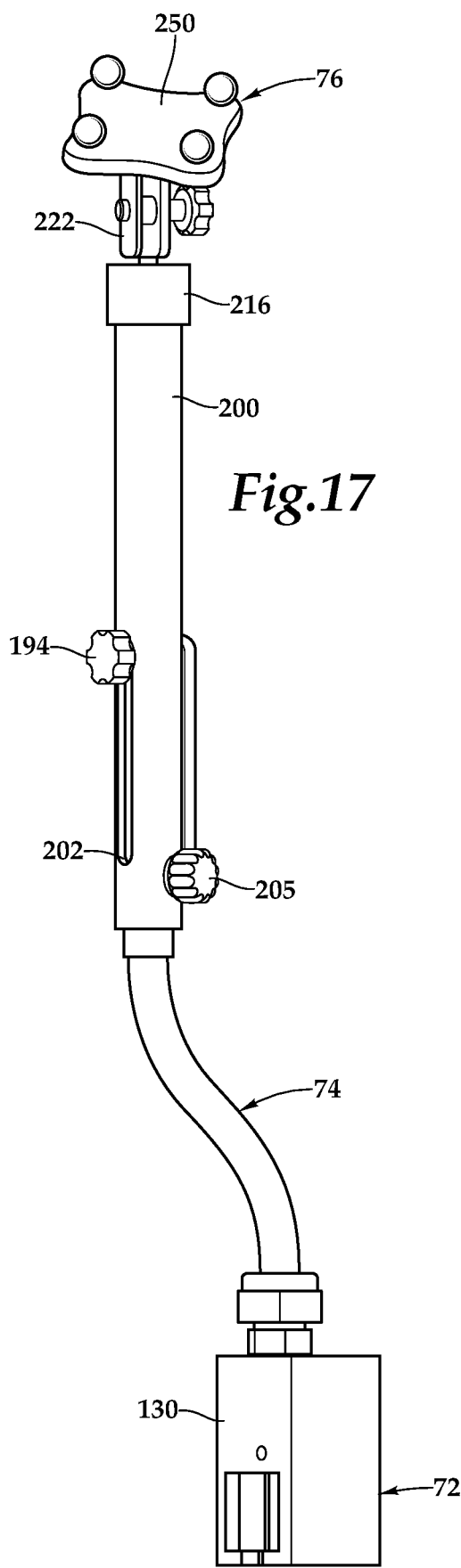
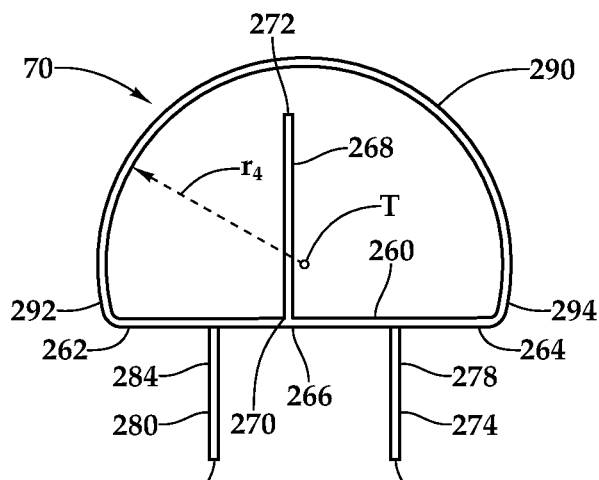
Fig.17
Fig.18

BASE STATION ASSEMBLY FOR AN OPERATING ROOM TABLE

PRIORITY STATEMENT & CROSS-REFERENCE TO RELATED APPLICATIONS

This application claims priority from U.S. Patent Application No. 63/382,685, entitled "Surgical Armrest" and filed on Nov. 7, 2022, in the name of Frederick H. Sklar; which is hereby incorporated by reference for all purposes.

This application discloses subject matter related to the subject matter disclosed in the following commonly owned, patent applications: U.S. patent application Ser. No. 18/502,795, entitled "Surgical Universal Headrest Including Skull Pin Holder Assembly" and filed on Nov. 6, 2023, in the name of Frederick H. Sklar; U.S. patent application Ser. No. 18/502,807, entitled "Surgical Universal Headrest Including Skull Pin Holder Assembly" and filed on Nov. 6, 2023, in the name of Frederick H. Sklar; U.S. patent application Ser. No. 18/502,811, entitled "Surgical Universal Headrest Including Skull Pin Holder Assembly" and filed on Nov. 6, 2023, in the name of Frederick H. Sklar; U.S. patent application Ser. No. 18/502,815, entitled "Surgical Universal Headrest Including Skull Pin Holder Assembly" and filed on Nov. 6, 2023, in the name of Frederick H. Sklar; U.S. patent application Ser. No. 18/502,820, entitled "Base Station Assembly for an Operating Room Table" and filed on Nov. 6, 2023, in the name of Frederick H. Sklar; U.S. patent application Ser. No. 18/502,839, entitled "Base Station Assembly for an Operating Room Table" and filed on Nov. 6, 2023, in the name of Frederick H. Sklar; U.S. patent application Ser. No. 18/502,841, entitled "Surgical Armrest" and filed on Nov. 6, 2023, in the name of Frederick H. Sklar; all of which are hereby incorporated by reference, in entirety, for all purposes.

TECHNICAL FIELD OF THE INVENTION

This invention relates, in general, to surgical appliances and, in particular, to a base station assembly used to support a surgical head holder and various surgical accessories during an operative procedure, such as an operative microsurgical procedure on the skull and brain.

BACKGROUND OF THE INVENTION

Multiple neurosurgical devices are readily available to support and secure the position of a patient's head during intracranial neurosurgery with safety and efficiency. Typical devices for adult patients use three or four high-pressure pins to exert enough force on the skull to both support the weight of the patient's head and prevent cranial movement. However, high-pressure pins are not safe for use with young children, infants, and babies, because the skulls of these young patients are thin and malleable; their heads are relatively large for their body-size; and the cranial sutures are open. In these children, high-pressure pins may fracture and penetrate the skull, displace bone fragments into the brain, or deform the skull as a ping pong fracture—the latter being common in newborns and young infants. These complications may destabilize the child's head on the headrest, thereby allowing it to move during a microsurgical procedure, or for the child to fall from the headrest during surgery. According to neurosurgical dogma, patients undergoing microsurgical intracranial operations require rigid skeletal fixation of the head to prevent cranial movement, which could be very dangerous during surgery. For these reasons, small infants and children are not considered candidates for state-of-the-art intracranial neurological surgery under the operating microscope, for example, nor can these children benefit from the effective use of image guidance technology, essentially declaring these young patients neurosurgically disabled, having been excluded from the benefits of progress of modern neurosurgery.

Important in a discussion of the mechanics of neurosurgery, an operative base station may function to connect a surgical head holder and various neurosurgical accessories, including brain retractors, a surgical armrest, and an image guidance reference frame to the operating room (OR) table. Ideally, the base station should be designed to maximize the functionality of each neurosurgical accessory without negatively impacting the others. For instance, the image guidance reference frame should be isolated on the base station and protected from being dislodged or moved unintentionally by a member of the surgical team, thereby disabling image guidance functionality for that surgery. On the other hand, the surgical head holder should functionally compliment the surgical base station to provide the surgeon a three-dimensional workspace in which positioning and re-positioning of brain retractors and a bimanual armrest are uncomplicated, easy, and efficient, thereby improving surgical safety and results. Accordingly, there is a need for an improved base station, not only to support a surgical headrest and the patient's head, but also to secure various surgical accessories that contribute greatly to the operative success of an intracranial surgical procedure, such as an operative procedure on the skull and brain.

SUMMARY OF THE INVENTION

It would be advantageous to achieve an advanced base station assembly to support a pediatric or adult neurosurgical headrest and various surgical accessories during a surgical procedure, such as an operative microsurgical procedure on the skull and brain. It would also be desirable to enable mechanical and medical-based solutions that would provide surgeon-controlled adjustability and mitigate spatial restrictions while providing enhanced surgeon control without requiring assistance of other OR personnel.

In one aspect, in some embodiments, a base station assembly for an operating room table is disclosed. In one embodiment, the base station assembly includes a predominantly circular base station that is secured to the operating room table. Attached to the base station at an adjustable distance from the OR table is a strong vertical member that provides the support of a neurosurgical head holder which is adjustably positioned relative to the support rod. Ideally, the support rod and therefore the head holder are concentric to the center axis of the base station. In addition, the base station includes an arcuate rail member with a selectively moveable clamp attached thereto. A vertical support arm extends from the selectively moveable clamp to provide selective attachment to a surgical accessory, such as a brain retractor, a surgical armrest, or a reference frame for intraoperative image guidance technology. The base station assembly provides complete adjustability to position the patient's head for best visualization and/or surgical approach to the pathology. In addition, the base station provides surgical accessory support that may be moved and adjusted by a surgeon at any time during an operation without contaminating the surgical field and without assistance from circulating operating room personnel.

The base station may include two concentric arcuate rail members. In one embodiment, the arcuate rail members are vertically offset and the radius of each of the two concentric arcuate rail members may differ. The selectively moveable clamp may include a body having rollers therein that are configured to be placed on either of the concentric arcuate rail members. A clamp pin and a finger lock are provided. In an open position, the clamp pin may be disengaged with the finger lock. In a closed position, the clamp pin may be engaged with the finger lock. The finger lock is forced into a braking relationship with the arcuate rail member in the closed position such that the finger lock prevents movement along the rail in the closed position.

The vertical support arm extends upward from the selectively moveable clamp. The vertical support arm may include an elongated member having a channel therethrough. A ball bearing train is located in the channel. A drive member is actuatable by a control knob to selectively switch an amount of mobility of the ball bearings within the elongated member between a lower mobility condition and a higher mobility condition by actuating between an engagement position and a release position, respectively. A clamp pin is located on the other end of the elongated member to actuate the selectively moveable clamp between the open position and the closed position. The actuation of the drive member actuates the clamp pin via the ball bearing train. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 8 is a ventral plan view of one embodiment of a drape holder depicted in FIG. 1;

FIG. 9 is a cephalic ventral perspective view, in partial cross-section, of a portion of the base station assembly depicted in FIG. 2;

FIG. 10B is a lateral elevation view, in partial cross-section, of a portion of the base station assembly depicted in FIG. 2 in a closed position;

FIG. 11B is a ventral plan view of a portion of the base station assembly depicted in FIG. 1 in a closed position;

FIG. 12 is a cephalic dorsal perspective view, in partial cross-section, of a portion of the base station assembly depicted in FIG. 2;

FIG. 13 is a cephalic dorsal perspective view of a portion of the base station assembly depicted in FIG. 2;

FIG. 14 is lateral elevation view, in partial cross-section, of a portion of the base station assembly depicted in FIG. 6;

FIG. 15 is a cephalic dorsal perspective view of a portion of the base station assembly depicted in FIG. 2;

FIG. 16 is a lateral perspective view of one embodiment of a portion of the base station assembly depicted in FIG. 2;

FIG. 17 is a lateral elevation view of a reference frame for intraoperative image guidance that would be attached to a base station assembly as depicted in FIG. 2;

FIG. 18 is a ventral plan view of another embodiment of a base station, the single rail base station, which may form a portion of the base station assembly depicted in FIG. 1, in a different implementation;

DETAILED DESCRIPTION OF THE INVENTION

Figure 1:
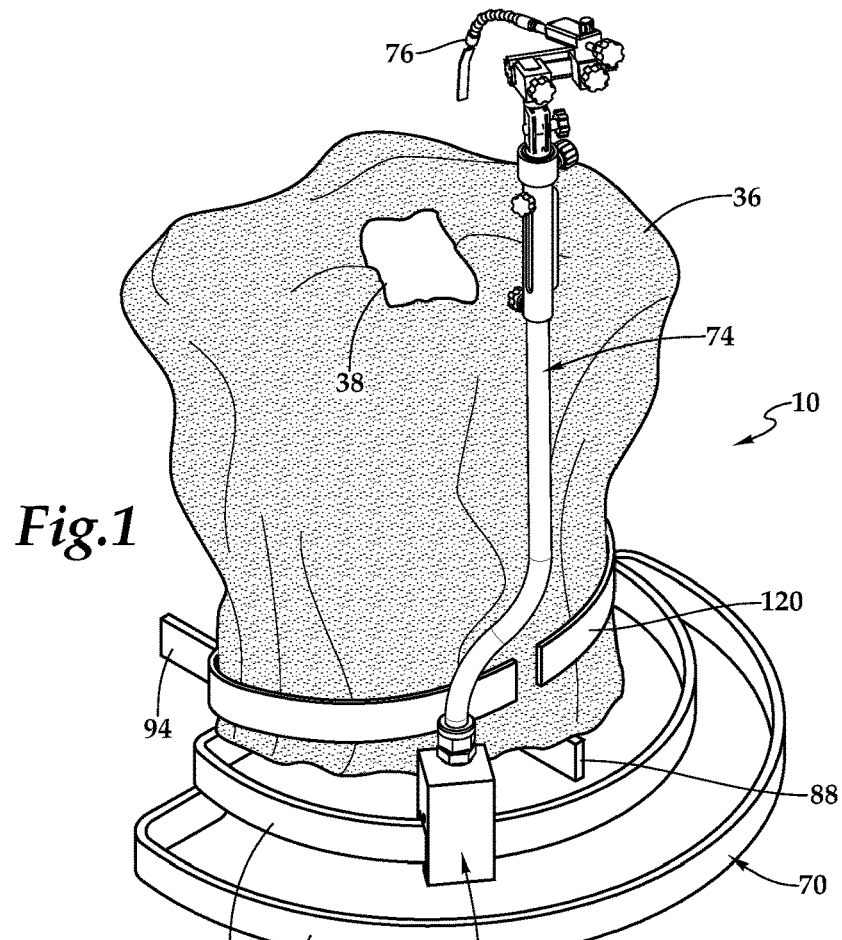
FIG. 1 is a cephalic dorsal perspective view of one embodiment of the cephalic end of an operating room table, to which the patient's head is secured and draped on a surgical head holder and base station assembly to do micro neurosurgery and to facilitate the use of various surgical accessories during a surgical procedure, such as an operative procedure on the skull and brain of a patient, according to the teachings presented herein.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIG. 1 through FIG. 6, therein is depicted one embodiment of a base station assembly 10 to support a surgical head holder 14 and various surgical accessories being utilized during surgical operations on the skull and brain of patient P. The base station assembly 10, the surgical head holder 14 with multiple low-pressure cranial pins for cranial stabilization, and the operating table 12 being the basic important components of a group of surgical tools required to provide stability of the patient's head for microsurgical operations as well as for utilization of image guidance technology on patients of nearly all sizes and ages.

Until recently, skeletal pin fixation could not be safely used with children under five (5) years of age with traditional neurosurgical headrests utilizing three (3) or four (4) pins at high pressures such as 70 lbs (or 45 lbs for so-called "pediatric" pins), because of the risks and incidence of serious complications. The skulls of this young children are simply too thin and flexible. The pins may fracture or deform the skull; they may penetrate and injure the brain or cause hemorrhage; the child may fall from the headrest during microsurgery. Now, there is a surgical headrest that can support the weight of a small child's head with a gel pad or gel pad assembly supraposed to the dorsal surface of the headrest, while cranial movement can be eliminated with multiple low pressure (finger-tightened) pins, because these latter pins are not supporting any of the weight of the head. To achieve cranial stability, this novel headrest may require 4 to 6 pins for an adult or teenager, 6 to 8 pins for a child, 8-10 pins for a newborn or small infant, and 10-12 pins, or more, for a premature infant.

That cranial stabilization with multiple low-pressure pins is no longer beyond the limitations of reasonable safety measures, microneurosurgery and image guidance technology can be done on nearly all patients of diverse ages and sizes, including premature infants. This surgical approach is not only applicable to neurosurgical operations but also be appropriate for use in some otolaryngological and orthopedic procedures as well.

The operating room table 12 provides the surgical equipment necessary on which a patient P lies during the surgical operation. As shown, the operating room table 12 includes an operating room table pad 18 supraposed to an operating room tabletop 20 including a support block 22 connected to a support block 24 by a horizontal support member 26. Vertical support members 28, 30 extend ventrally from the support block 24 with the vertical support member 28 having a support block 32 and the vertical support member 30 having a support block 34. The support blocks 22, 24, 32, 34 may each be selectively adjustable with knobs (not shown) to assist the surgical staff with proper alignment and placement of the components of the base station assembly 10, the surgical head holder 14, and various surgical accessories on the operating room table 12. By way of example, the support blocks 32, 34 provide for alignment and placement in the dorsal-ventral direction as well as the caudal-cephalic direction. As shown, a surgical drape 36 is positioned over the entire operating room table 12 as well as the head of the patient P. The surgical drape 36 has a surgical field opening 38 providing access to the head or other body part of the patient P. It should be appreciated that although one embodiment of the operating room table 12 is illustrated and described, the teachings presented herein are applicable to other operating room table configurations and designs.

The surgical head holder 14 includes a headrest 40, which may be a universal headrest, that generally functions in a plane approximately parallel to the top of the operating room table 12; although, the headrest 40 may be tilted in any direction as necessary. The headrest 40 with appropriate gel pads carries the weight of the head of the patient P. The surgical head holder 14 includes a skull pin holder assembly 42 having skull pin holders 44, 46, 48, 50, 52, 53, or more, depending on the thinness of the patient's skull. Utilizing multiple low-pressure (finger-tightened) pins, the skull pin holder assembly 42 contributes to preventing any movement of the head of the patient P, thereby allowing safe microsurgery and enabling accurate employment of image guidance technology. As shown, the headrest 40 is supported by a support block 54 having a vertical support member 56 extending therefrom that connects to the base station assembly 10 with the use of a support block 58. The support blocks 54, 58 may each be selectively adjustable with knobs (not shown) to assist the surgical staff with proper alignment and placement of the components of the surgical head holder 14. It should be appreciated that although one embodiment of the surgical head holder 14 is illustrated and described, the teachings presented herein are applicable to other operating room table configurations and designs.

Referring now to FIG. 1 through FIG. 8, in some embodiments, the base station assembly 10 includes a base station 70 having a selectively moveable clamp 72 attached thereto. The selectively moveable clamp 72 has a vertical support arm 74 extending therefrom. The vertical support arm 74 may include a short, tight "S" curve S to assist in positioning of the vertical support arm 74 and a surgical accessory 76 attached thereto. That is, the vertical support arm 74 extends from the selectively moveable clamp 72 to provide selective attachment of the surgical accessory 76 such as a retractor arm, a surgical armrest, or an image guidance frame, for example. In one implementation, the base station 70 includes a horizontal support member 80 having ends 82, 84 with a midpoint 86 therebetween. A horizontal support member 88 has ends 90, 92. The end 90 of the horizontal support member 88 is coupled to the midpoint 86 of the horizontal support member 80 such that the horizontal support member 88 is perpendicular to the horizontal support member 80 and secured to the horizontal support member 80 at a position offset from a center T. A horizontal support member 94 includes ends 96, 98 with the end 98 being connected to the horizontal support member 80 between the end 82 and the midpoint 86. As shown, the horizontal support member 94 extends caudally from the horizontal support member 80 such that the horizontal support member 94 is perpendicular to the horizontal support member 80. Similarly, a horizontal support member 100 includes ends 102, 104 with the end 104 being connected to the horizontal support member 80 between the end 84 and the midpoint 86. As shown, the horizontal support member 100 extends caudally from the horizontal support member 80 such that the horizontal support member 100 is perpendicular to the horizontal support member 80. The horizontal support members 94, 100 of the base station 70 join the base station assembly 10 to the operating room table 12. More particularly, in one embodiment, the horizontal support member 80 is joined to the vertical support member 28 at the support block 32 and the horizontal support member 100 is joined to the vertical support member 30 at the support block 34.

An arcuate rail member 106, which may be an upright bar in cross-section, includes a radius $r_1$, as measured from the center T, and ends 107, 108. The end 107 is coupled to the end 82 of the horizontal support member 80 and the end 108 is coupled to the end 84 of the horizontal support member 80. The vertical support member 56 is secured to the horizontal support member 88, which is off center with respect to the center T, such that the vertical support member 56 is positioned at the center T. In turn, the surgical head holder 14 and the headrest 40 are positioned at the center T with various surgical accessories positionable and repositionable, at the surgeon's discretion, via the base station assembly 10 around the center T.

A second arcuate rail member 110, which may also be an upright bar in cross-section, includes a radius $r_2$, as measured from the center T, and ends 111, 112. The end 111 is coupled to the end 82 of the horizontal support member 80 at a ventral tab 114 and the end 112 is coupled to the end 84 at a ventral tab 116 of the horizontal support member 80. The use of the ventral tab 114 and the ventral tab 116 permit the arcuate rail member 106 and the arcuate rail member 110 to be vertically offset. For example, placement of the selectively moveable clamp 72 specialized as necessary to fit on ventral tab 114 or ventral tab 116 may, one or the other, provide an ideal location to attach the reference frame required for image guidance as depicted in FIG. 17. Importantly, as shown, a passage 125 is located between the horizontal support member 88 and the arcuate rail member 106 to provide for the movement of the selectively moveable clamp 72 around the orbit of the arcuate rail member 106.

In one implementation, the arcuate rail member 106 and the second arcuate rail member 110 are concentric. Further, the radius $r_2$ of the arcuate rail member 110 is greater than the radius $r_1$ of the arcuate rail member 106. In one embodiment of the base station 70, the arcuate rail member 106 may have an arc of about 190 degrees to about 200 degrees. In one particular embodiment of the base station 70, the arcuate rail member 106 may have an arc of about 195 degrees. In one embodiment of the base station 70, the arcuate rail member 110 may have an arc of about 205 degrees to about 215 degrees. In one particular embodiment of the base station 70, the arcuate rail member 110 may have an arc of about 210 degrees. As will be discussed in additional detail hereinbelow, it should be appreciated that, depending on the embodiment selected by the surgeon, the base station 70 may have one arcuate rail member, i.e., arcuate rail member 106 or arcuate rail member 110, or the base station 70 may have two arcuate rail members, i.e., arcuate rail members 106, 110.

As shown, the bottoms of the surgical drape 36 that fall naturally from the draping of the head of the patient are gathered and tucked inside a drape holder 120 having an arcuate space 122 defined by rostral retaining members 124, 126, and caudal retaining member 130. The drape holder 120 is adjustably secured to the vertical support member 56 by a support member 128. In one embodiment, the radius $r_3$ of the drape holder 120 is less than the radius $r_1$ of the rail member 106 and the radius $r_2$ of the rail member 110. This permits the surgical drape 36 to be gathered and groomed so as not to interfere with the surgical procedure or use of the base station assembly 10.

Referring now to FIG. 9 through FIG. 13, in some embodiments, the selectively moveable clamp 72 includes a body 130 having an upper end 132 and a lower end 134. The body 130 includes a rail frame 136 and a rail frame 138. Rollers 140, 142 are secured to the rail frame 136 and configured to be placed on the arcuate rail member 106 or in a different implementation, the arcuate rail member 110. Similarly, rollers 144, 146 are secured to the rail frame 138 and configured to be placed on the arcuate rail member 106 or in a different implementation, the arcuate rail member 110. As shown, the roller 140 may appose the roller 144 and the roller 142 may appose the roller 146. The body 130 has a distance d between the rollers 140, 144 and the rollers 142, 146, which is set to accommodate a width of a rail in the form of the arcuate rail member 106 of the base station 70 or, alternatively, the arcuate rail member 110 of the base station.

Figures 10A, 11A:
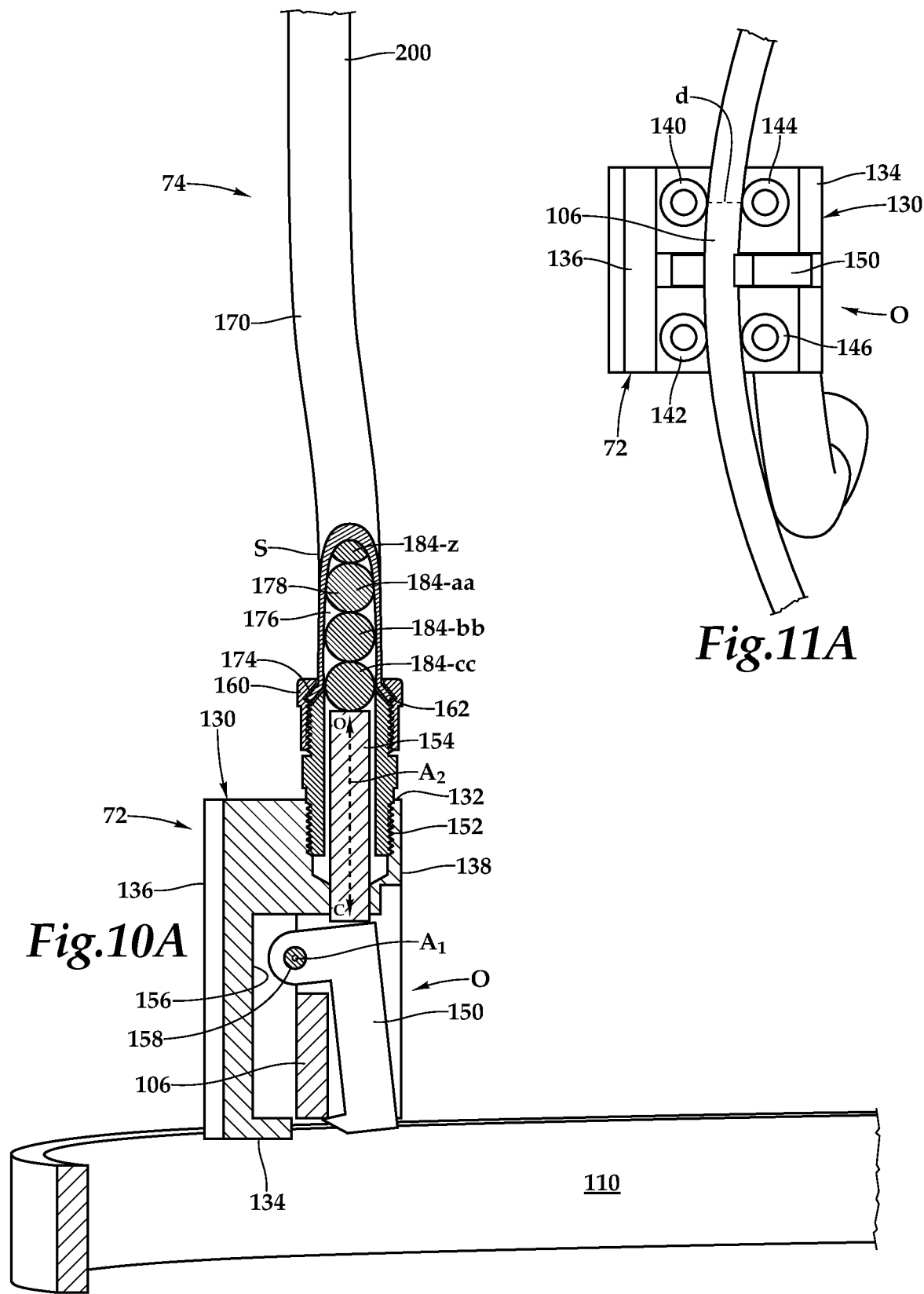
FIG. 10A is a lateral elevation view, in partial cross-section, of a portion of the base station assembly depicted in FIG. 2 in an open position.
FIG. 11A is a ventral plan view of a portion of the base station assembly depicted in FIG. 1 in an open position.

A finger lock 150 is coupled to the body 130 for pivoting movement in a mandibular motion relative to the rail frame 136 about an axis $A_1$ parallel to a tangent of the arcuate rail member 106. The axis $A_1$ may be parallel to the floor of the operating room. The finger lock 150 is configured to be placed in a braking relationship with the arcuate rail member 106 to prevent movement of the selectively moveable clamp 72 on the arcuate rail member 106. In some embodiments, the braking relationship is achieved exerting enough pressure and friction between the finger lock 150 of the selectively moveable clamp 72 on the arcuate rail member 106 or the arcuate rail member 110 when the finger lock 150 is in the closed position, thereby preventing movement of the selectively moveable clamp 72. When the finger lock 150 is released from the arcuate rail member 106, movement of the selectively moveable clamp 72 is facilitated by rollers 140, 142, 144, 146 thereon the arcuate rail member 106. A receiving member 152, which may be in the form of a lock screw, for example, intersects the body 130 at the upper end 132 and the receiving member 152 retains a clamp pin 154. As shown, the clamp pin 154 is located suprajacent the finger lock 150 with axial movement about an axis $A_2$ perpendicular to the axis $A_1$. The clamp pin 154 is configured to actuate the finger lock 150 between an open position O and a closed position C. In the open position O, as shown in FIGS. 10A and 11A, the clamp pin 154 is disengaged with the finger lock 150 and, in the closed position C, as shown in FIGS. 10B and 11B, the clamp pin 154 is engaged with the finger lock 150. Further, in the open position, the finger lock 150 does not make strong contact with the arcuate rail member 106 and the rollers 140, 142, 144, 146 are permitted to move along the arcuate rail member 106. On the other hand, in the closed position C, the finger lock 150 is forced into the braking relationship with the arcuate rail member 106, and the rollers 140, 142, 144, 146 are inhibited from moving along the arcuate rail member 106. Similarly, the selectively moveable clamp or clamps 72 positioned on the arcuate rail member 110 show analogous braking and release features as discussed.

The rail frames 136, 138 may define a chamber 156 and the finger lock 150 is coupled to the body 130 for pivoting movement by a pivot pin 158 which extends from the body 130 into the chamber 156. In this configuration, the clamp pin 154 may extend into the chamber 156 to engage the finger lock 150 in the closed position C. In operation, in the open position O, the rollers 140, 142, 144, 146 facilitate movement of the selectively moveable clamp 72 along the rail, which may have an arcuate form with a rectangular cross-section, for example, and, as illustrated includes the arcuate rail member 110. It should be appreciated, however, that the rail may take the form of the arcuate rail member 106 as well.

Referring now to FIG. 3, FIG. 4, FIG. 5, FIG. 9, FIG. 10A, FIG. 10B, and FIG. 14, in some embodiments, the vertical support arm 74 includes an elongated member 170 having ends 172, 174 with a channel 176 therethrough. A ball bearing train 178 is located in the channel 176 from proximate the end 172 to proximate the end 174. The ball bearing train 178 has an upper end 180 proximate the end 172 and a lower end 182 proximate the end 174. As shown, the ball bearing train 178 includes multiple ball bearings 184-$a$, 184-$b$, 184-$c$, 184-$d$, 184-$e$, 184-$f$, 184-$g$, 184-$h$, 184-$i$, 184-$j$, 184-$k$, 184-$l$, 184-$m$, 184-$n$, 184-$o$, 184-$p$, 184-$q$, 184-$r$, 184-$s$, 184-$t$, 184-$u$, 184-$v$, 184-$w$, 184-$x$, 184-$y$, 184-$z$, 184-$aa$, 184-$bb$, 184-$cc$ being disposed in an angular contact, tandem arrangement. It should be appreciated that the number of ball bearings may vary depending on the construction and application of the vertical support arm 74.

A drive member 186 is located proximate the end 172 of the elongated member 170 and the drive member 186 is configured to selectively actuate an amount of flexibility of the ball train within the elongated member 170 between a lower flexibility condition and a higher flexibility condition, which enables not only 360° rotation, but also angular adjustment of the elongated member 170 relative to its receiving member 152 at joint 162. The curve S of the elongated member 170 amplifies simple rotation into a maximal radial displacement equal to the offset of the curve S. In addition, the elongated member 170 can be tilted up to about 7° by tilting the terminal flange of end 174 within the wedge-shaped joint 162, and then actuating between a release position to an engagement position of drive member 186. As best seen in FIG. 10A and FIG. 10B, the receiving member 152 includes the end cap 160 at the joint 162. As shown the elongated member 170, which may have a flanged tip at its lower end 174, is interposed between the receiving member 152 and the end cap 160 at the joint 162 such that the elongated member 170 can be rotated and/or pivoted at joint 162. That is, in some embodiments, the elongated member 170 may be manufactured with a curve S built into the elongated member 170. Accordingly, in the higher flexibility condition, the elongated member may be moved, rotated, and/or tilted into the desired position, which can then be held in place at the joint 162, by actuating the lower flexibility condition of drive member 186. Such manipulation may be utilized to reposition the elongated member 170. Tilting the elongated member 170 at joint 162 provides more subtle positional adjustment.

As previously alluded, the clamp pin 154 is located proximate the end 174 of the elongated member 170 and the clamp pin 154 is configured to actuate the selectively moveable clamp 72 between the open position O and the closed position C. In the release position, the drive member 186 is disengaged from the upper end 180 of the ball bearing train 178; and in the release position, the ball bearing train 178 is disengaged from the clamp pin 154 to actuate the selectively moveable clamp 72 to the open position O. Above the S-shaped curve at the proximal end of the elongated member 170, the elongated member 170 may include a vertical axis $A_3$ with the ball bearing train 178 having relative axial movement about the vertical axis $A_3$ with the drive member 186 in the release position.

On the other hand, in the engagement position, the drive member 186 is engaged with the upper end 180 of the ball bearing train 178 to limit freedom of movement between the ball bearings 184-$a$ through 184-$cc$. Further, in the engagement position, the ball bearing train 178 is engaged with the clamp pin 154 to actuate the selectively moveable clamp 72 to the closed position via the finger lock 150.

An upper end cap 188 may be coupled to the end 172 of the elongated member 170. The upper end cap 188 may have an interior 190 and an exterior 192 and the drive member 186 may be housed within the interior 190 of the upper end cap 188. As shown, a control knob 194 may be housed within the upper end cap 188 and be selectively actuatable from the exterior 192 of the upper end cap 188. The control knob 194 translates a rotation of the control knob 194 to a movement of the drive member 186. An attachment member 198, which may be selectively telescoping, may be secured to the upper end cap 188 to provide selective attachment to the surgical accessory 76, such as a medical device selected from the group consisting of retractor arms, armrests, and the reference frame for image guidance at a coupling joint 196. In particular, in the application of certain medical devices, at the end 172 of the elongated member 170, the attachment member 198 may include a cylindrical sheath 200 having a slot 202 to accommodate the control knob 194. A cabined recess 204 may be positioned opposite to the slot 202 to accept and house the drive member 186, which extends from the control knob 194. A hand adjustment knob 205 controls an adjustability, i.e., a telescoping extension and retraction of the attachment member 198 as shown by double-headed arrow U-D (see FIG. 5). In one embodiment, the cylindrical sheath 200 may be made of metal and be approximately 20 cm (7.8 in) in length, which contains the slot 202, such as 12 cm (4.7 in) to accommodate the control knob 194. In this way, the height of the vertical support arm 74 can be extended and then locked in place with the hand adjustment knob 205.

In one embodiment, as mentioned, the drive member 186 extends from the control knob 194. The drive member 186 may include a threaded section 206 connected to a conical section 208 connected to an end shank 210. The threaded section 206 may be inserted through the slot 202 and threadedly engaged with a threaded opening 212 which traverses the elongated member 170 and the upper end cap 188. The conical section 208 engages the ball bearing train 178 at the upper end 180 thereof. Engagement of the conical section 208 with the ball bearing 184-$a$ increases the downward force applied to the ball bearing train 178 resulting in the engagement position. On the other hand, disengagement of the conical section 208 decreases the downward force applied to the ball bearing train 178 resulting in the release position. The end shank 210 traverses an opening 214 which passes through the elongated member 170 and the upper end cap 188 and exits the elongated member 170 and the upper end cap 188 into the cabined recess 204 of the cylindrical sheath 200.

Referring now to FIG. 14 through FIG. 16, the elongated member 170 is configured to selectively actuate between the release position and the engagement position by actuation of the control knob 194. In the release position, the selectively moveable clamp 72 is actuated to an open position where the selectively moveable clamp 72 may slide on the arcuate rail member 106—or arcuate rail member 110—to be repositioned. On the other hand, in the engagement position, the selectively moveable clamp 72 is in the closed position and locked in position on the arcuate rail member 106—or arcuate rail member 110. The cabined recess 204, which is depicted as presenting a bulge, may be positioned opposite to the slot 202 to accept and house the end shank 210 of the control knob 194. The hand adjustment knob 218 may provide rotary adjustment of a ring member 216. Attachment to the ring member 216 of the vertical support arm 74 provides a coupling to the surgical accessory 76. More particularly, the ring member 216 is set over the cylindrical sheath 200 in a circumscribing manner. As mentioned, hand adjustable knob 218 tightens or loosens the ring member 216 to allow rotational adjustment around the vertical support arm 74. The top of the ring member 216 is closed and supports a metal ball 220 attached at its dorsal center. The metal ball 220 is the bottom ball of a two-ball-joint clamp 222 having a knob 223 and is adjustably oriented in a more or less vertical position. A metal ball 224 serving as an upper ball of the two-ball-joint clamp 222 arises from the inferior surface of a device clamp 226 having a knob 227, to which a surgical accessory 76, such as a brain retractor arm, an armrest, or an image guidance reference frame, for example, can be attached. As shown in FIGS. 15 and 16, a rail support member 228 may hold one or multiple brain retractor devices.

The rail support members 228 may be chosen from a variety of lengths and/or geometries according to the patient's size, surgical positioning, as well as the preference of the surgeon. The rail support member 228 may be angled with a double-T-profile defining tracks 230, 232. A brain retractor arm 234 having a body 236 with a flexible arm 238 extending therefrom is secured to the track 230. A clamp 240, under the control of a positioning knob 242, extends from the body 236 and ensures the adjustable securement to the track 230 and minor repositioning of the brain retractor arm 234 as shown by arrows $M_2$, $M_3$. A tension knob 244 provides control of the flexible positioning in the flexible arm 238. A pivot knob 246 provides axial control. On the other hand, one or more additional retractor arms can be attached to a single rail support member 228 to facilitate simultaneous use of multiple brain retractors in close proximity—three brain retractors in FIG. 16, for instance.

Referring now to FIG. 17, by way of example, the base station assembly 10 may include the selectively moveable clamp 72 attached thereto with the vertical support arm 74 extending therefrom. The vertical support arm includes the elongated member 134. A reference frame 250 for intraoperative image guidance is secured to the two-ball-joint clamp 222 of the vertical support arm 74. FIG. 17 shows the cylindrical sheath 200 having been modified for specific use with the image guidance reference frame 250. The adjustment knobs 194, 205 have been lowered below the level of operative sterility, so that none of the surgical participants—doctors, nurses, and OR technicians—be tempted accidentally to "adjust" the position of the reference frame, thereby disabling image guidance. Once the position of the reference frame has been provided to the image guidance computer (prior to prepping and draping), there is never a reason to change the position of the frame.

Referring now to FIG. 18, in another implementation, the base station 70 includes a horizontal support member 260 having ends 262, 264 with a midpoint 266 therebetween. In this implementation, a single orbit for the selectively moveable clamp 72 is provided as compared to the two orbits presented in FIG. 5, for example. A horizontal support member 268 has ends 270, 272. The end 270 of the horizontal support member 268 is coupled to the midpoint 266 of the horizontal support member 260 such that the horizontal support member 268 is perpendicular to the horizontal support member 260. A horizontal support member 274 includes ends 276, 278 with the end 278 being connected to the horizontal support member 260 between the end 262 and the midpoint 266. The horizontal support member 274 may extend caudally from the horizontal support member 260 such that the horizontal support member 274 is perpendicular to the horizontal support member 260. Similarly, a horizontal support member 280 includes ends 282, 284 with the end 284 being connected to the horizontal support member 260 between the end 264 and the midpoint 266. As shown, the horizontal support member 280 may extend caudally from the horizontal support member 260 such that the horizontal support member 280 is perpendicular to the horizontal support member 260. The horizontal support members 274, 280 of the base station 70 join the base station assembly 10 to the operating room table 12. An arcuate rail member 290, which may be an upright bar, includes a radius $r_4$ and ends 292, 294. The end 292 is coupled to the end 262 of the horizontal support member 260 and the end 294 is coupled to the end 264 of the horizontal support member 260.

Figure 19A:
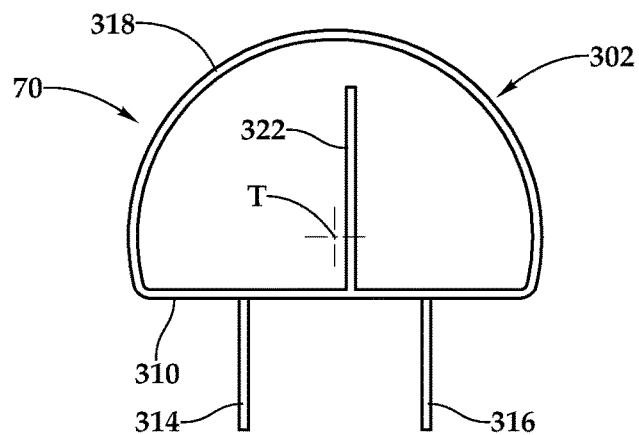
FIGS. 19A through 19C respectively represent a composite of ventral plan views of three base station embodiments, including a single rail device, a double rail device, and a larger center-point device; each with the center points of the arcuate rails being indicated.
Figure 19B:
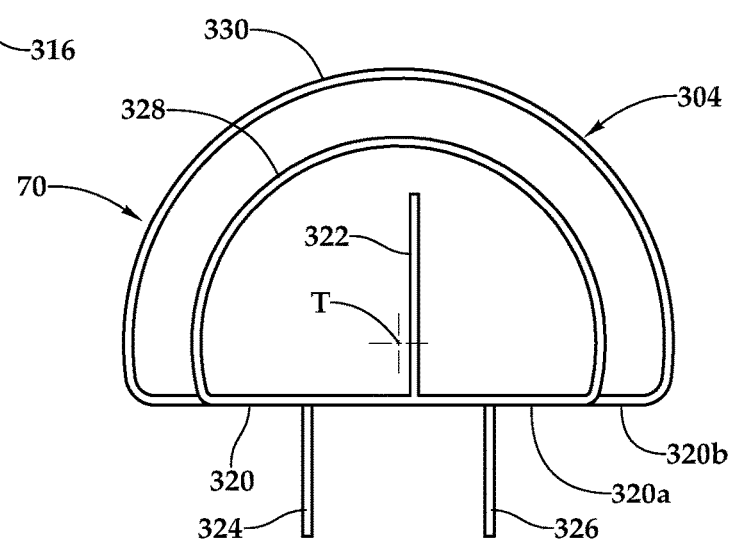
Figure 19C:
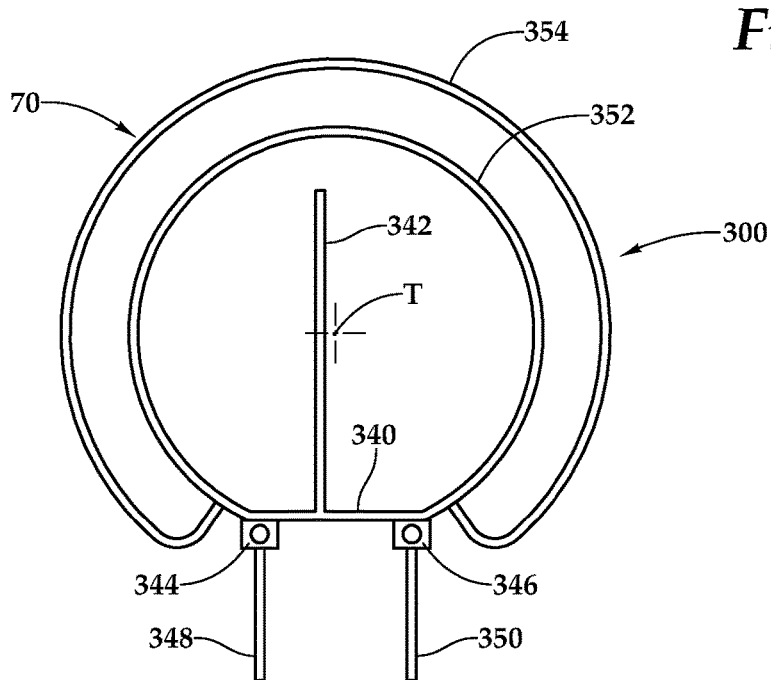

Referring now to FIGS. 19A, 19B, and 19C, as previously mentioned, other embodiments of the base station assembly 10 are within the teachings presented herein. In one such embodiment, the base station assembly 10 may have a larger presentation as indicated by center-point configuration 300. In FIGS. 19A, 19B, and 19C, the relative footprints of a single rail base station 302, a double rail base station 304, and the center-point base station 300 are comparatively shown together, utilizing the same scale.

Referring now to FIG. 19A, in another implementation, which is similar to the configuration introduced in FIG. 18, the base station 70 includes a horizontal support member 310. In this implementation, a single orbit for the selectively moveable clamp 72 is provided as compared to the two orbits presented in FIGS. 5 and 6, for example. A horizontal support member 312 is coupled the horizontal support member 310 such that the horizontal support member 322 perpendicular to the horizontal support member 310. Horizontal support members 314, 316 of the base station 70 join the base station assembly 10 to the operating room table 12. An arcuate rail member 318 is coupled to the horizontal support member 310.

Figure 7:
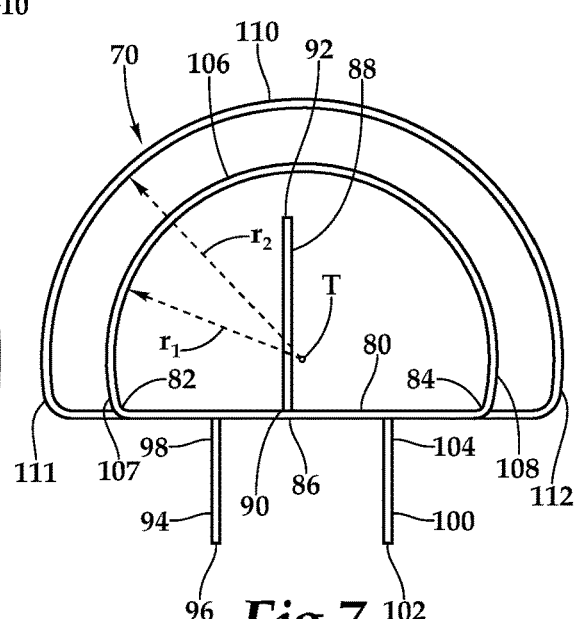
FIG. 7 is a ventral plan view of one embodiment of a base station, which forms a portion of the base station assembly depicted in FIG. 2.

Referring now to FIG. 19B, in another implementation, which is similar to the configuration introduced in FIG. 7, the base station 70 includes a horizontal support member 320, which may include horizontal support submembers 320-a, 320-b. A horizontal support member 322 is coupled to the horizontal support member 320 such that the horizontal support member 322 is perpendicular to the horizontal support member 320. Horizontal support members 324, 326 of the base station 70 join the base station assembly 10 to the operating room table 12. Arcuate rail members 328, 330 are coupled to the horizontal support member 320, in this implementation, to provide two orbits for the selectively moveable clamp 72.

Referring now to FIG. 19C, in another implementation, which is similar to the configuration introduced in FIG. 7, the base station 70 includes a horizontal support member 340. A horizontal support member 342 is coupled to the horizontal support member 340 such that the horizontal support member 342 is perpendicular to the horizontal support member 340. Blocks 344, 346 have horizontal support members 348, 350 of the base station 70 to join the base station assembly 10 to the operating room table 12. In this implementation, arcuate rail members 352, 354 are coupled to the horizontal support member 340 to provide two orbits for the selectively moveable clamp 72.

Figure 20:
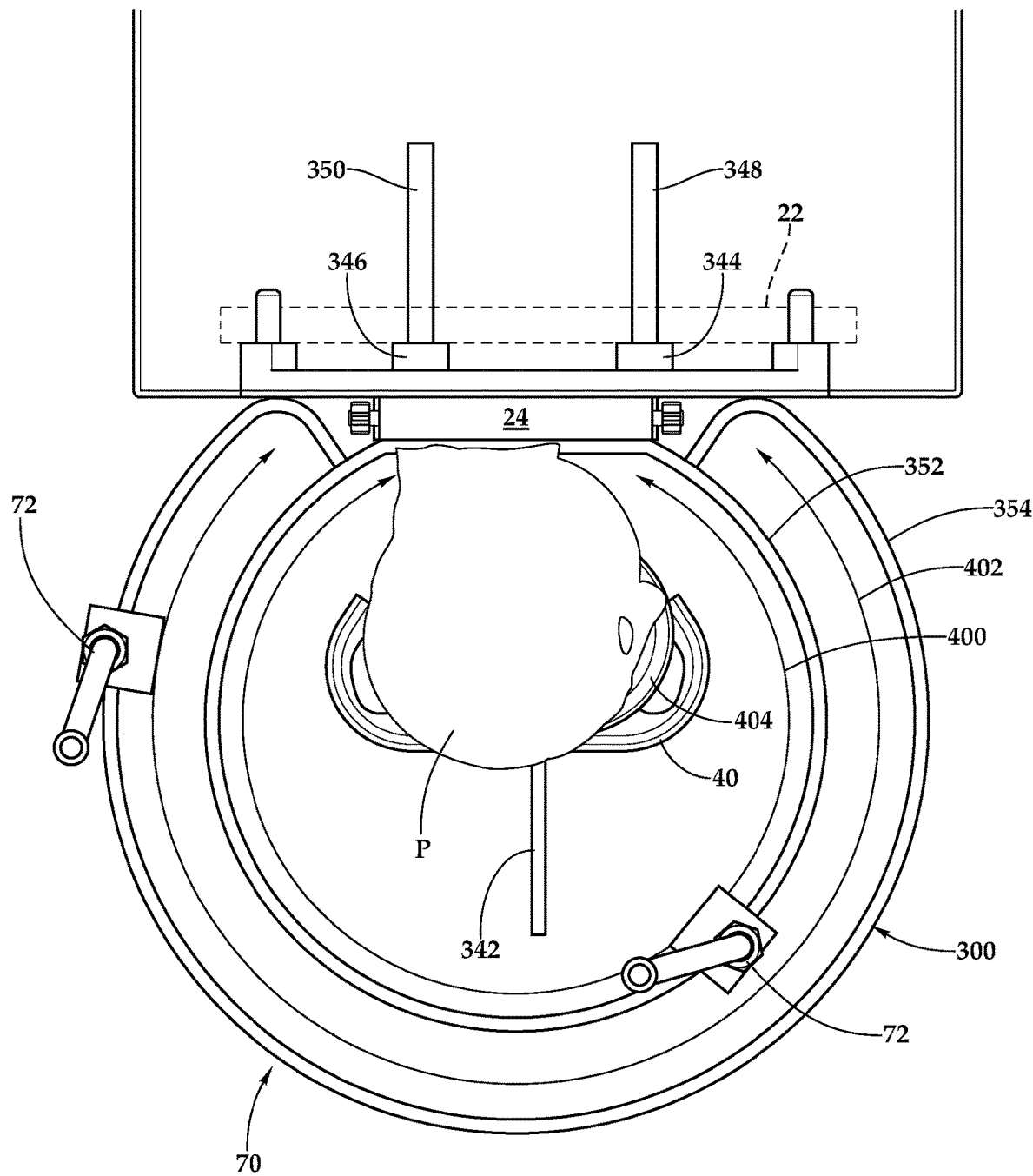
FIG. 20 is a top plan view of the larger center-point base station depicted in FIG. 19C, on which an adult patient is represented in a lateral surgical position on the surgical head holder (without skull pin fixation for clarity), wherein a selectively moveable clamp being attached to each of two concentric arcuate rails with maximal clamp excursions on the rails being indicated by arrows.
Figure 22:
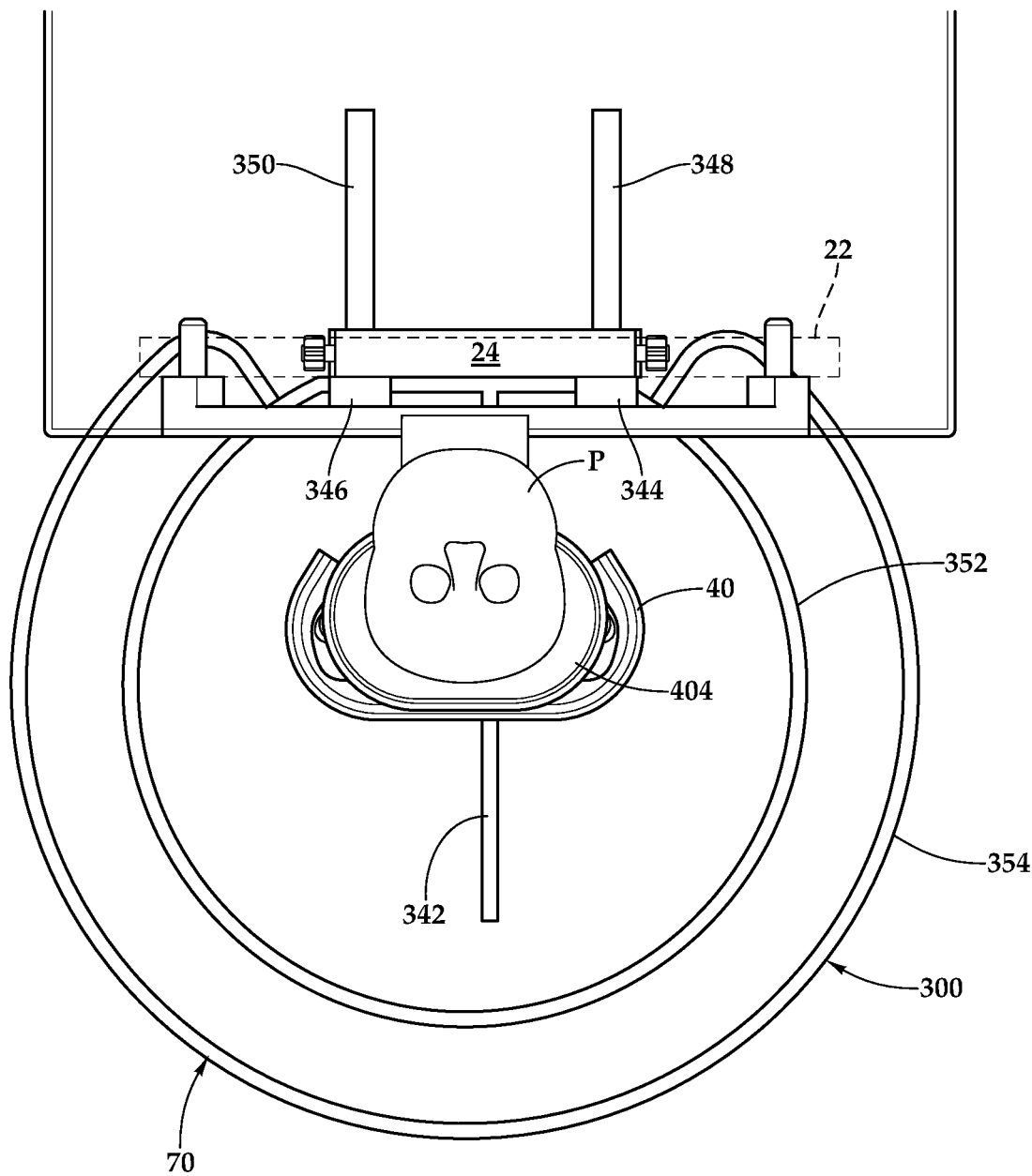
FIG. 22 is a top plan view of the surgical head holder and a four (4)-month-old patient, both supported by a center-point base station of which the cross bar (shown with two (2) side tightening knobs) has been adjustably moved caudally, causing the OR table to overlap the base station.
Figure 23:
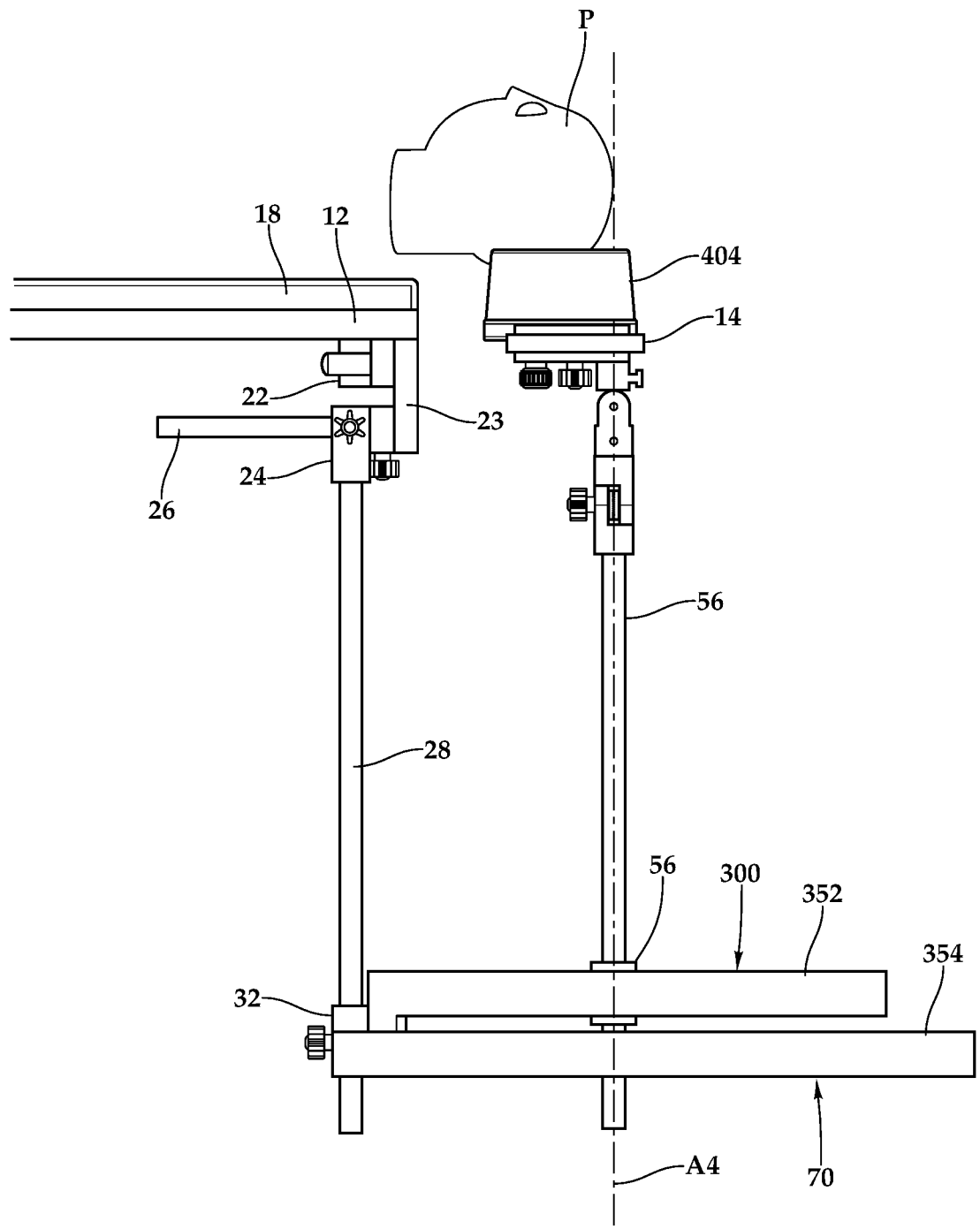
FIG. 23 is a lateral elevation view of the base station supporting the four (4)-month-old child depicted in FIG. 22 in which the cross bar (shown with the six-star knob) has been adjustably moved to be adjacent to the caudal aspect of the table connecting device, thereby causing the OR tabletop to overlap the base station.
Figure 24:
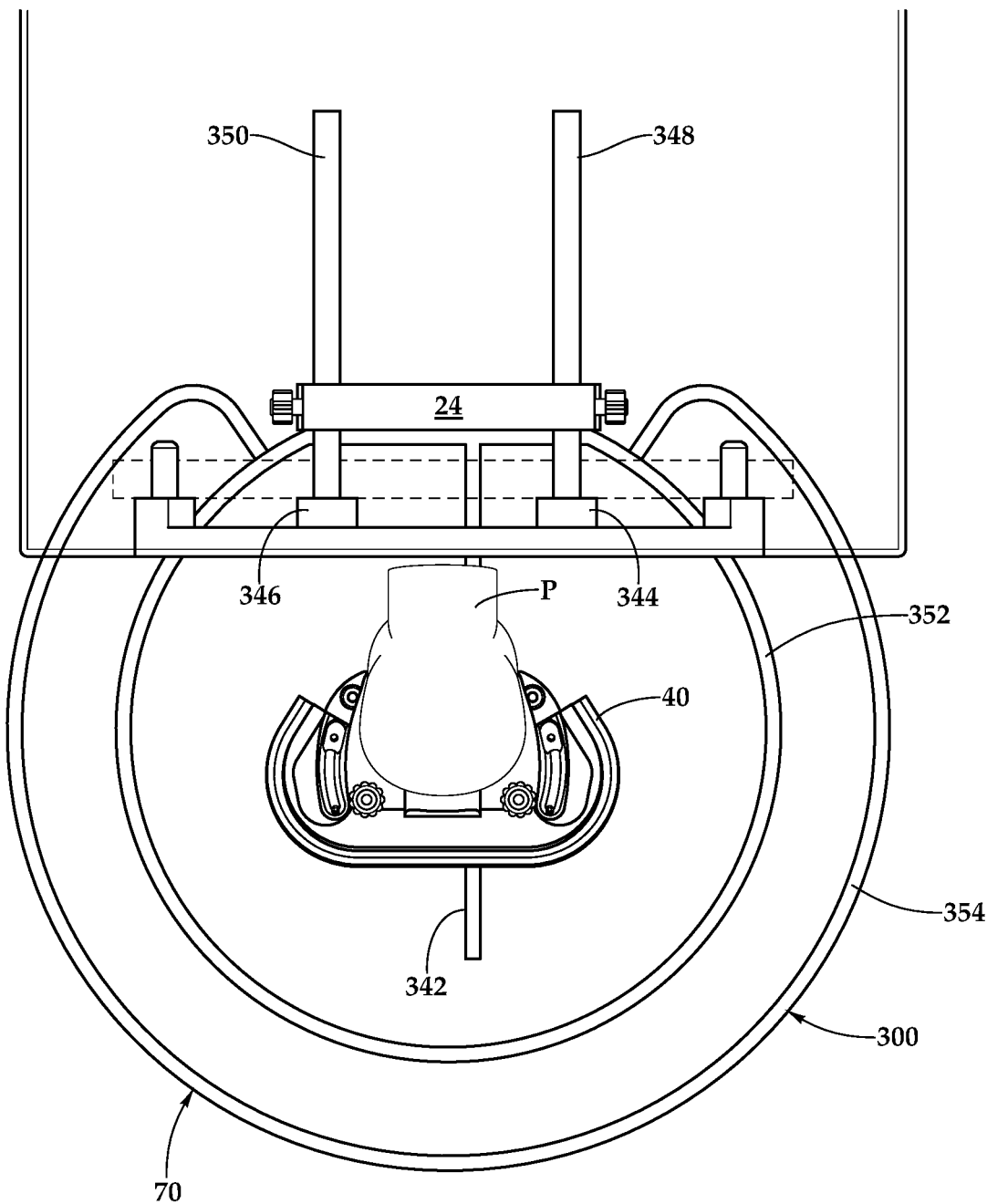
FIG. 24 is a top plan view of forty (40)-week gestational age newborn positioned prone on the surgical head holder supported by a center-point base station on which the cross bar (shown with two [2] side tightening knobs) has been additionally and adjustably moved caudally, further from the table connecting device, causing the OR tabletop to overlap a larger portion of the base station.
Figure 25:
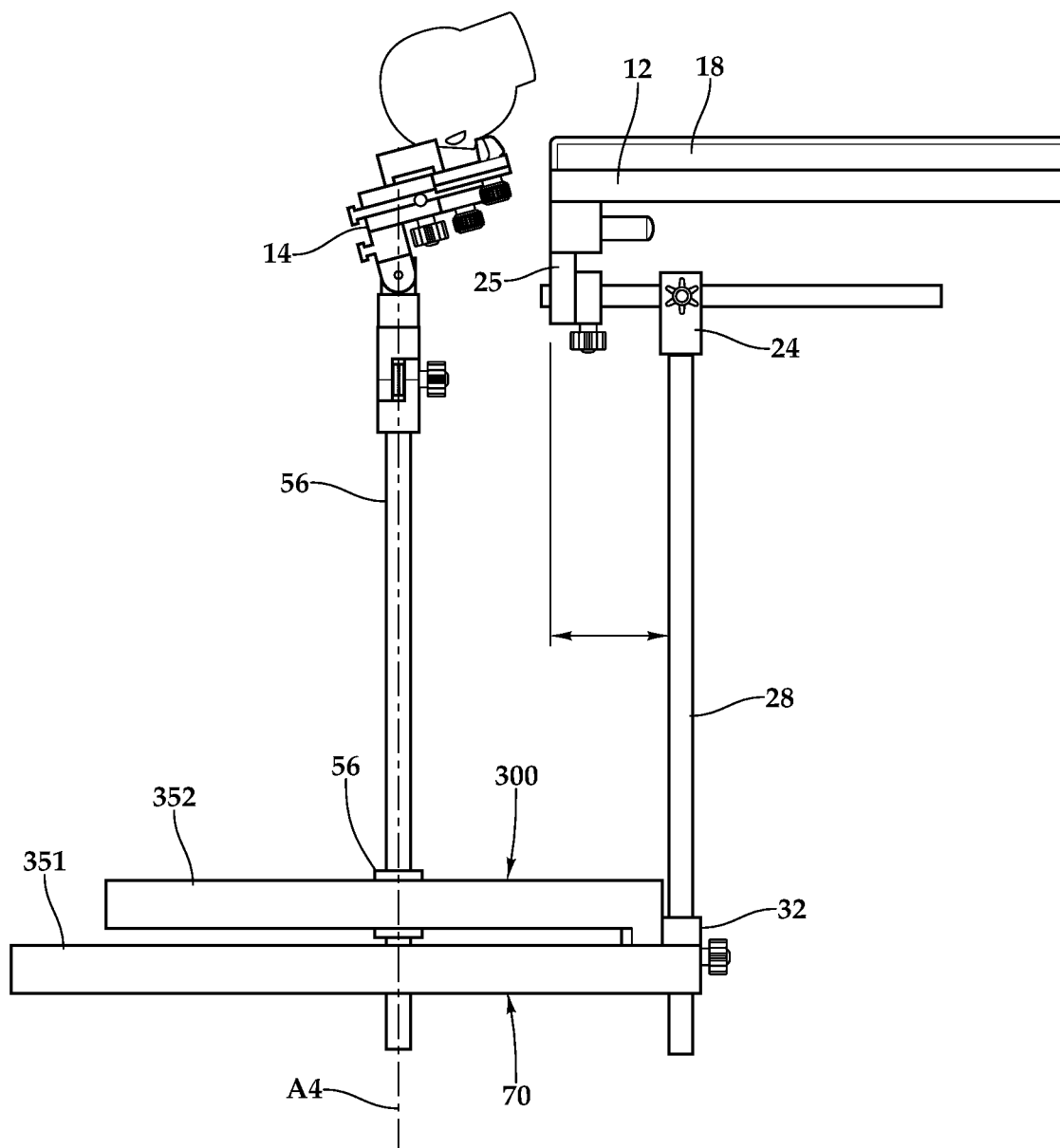
FIG. 25 is a lateral elevation view of the base station supporting the forty (40)-week gestational age patient in the prone position as depicted in FIG. 24, in which the crossbar has been adjustably and caudally moved, thereby causing the OR tabletop to overlap a larger portion of the base station.

That is, as shown in FIG. 19C, in some implementations of this embodiment of the base station 70, arcuate rails of the same 9" (22.86 cm) and 12" (30.48 cm) radiuses as the double rail embodiment depicted in FIG. 7 are presented. This larger embodiment of base station 70 in FIG. 19C encompasses a greater portion of a complete circle, and the respective arcuate rail members 106, 110 may have arcs of 308.5 degrees and 276.2 degrees, for example, thereby significantly increasing the potential arcuate excursion distances for selectively moveable clamps 72. Moreover, as illustrated in FIGS. 20, 22, and 24, an additional advantage of this embodiment allows the base station 70 to be positioned partially underlapping the rostral end of the OR table. This can be easily accomplished by re-positioning the cross bar 24 of the base station 70 from its usual position just rostral to the "W" shaped connection bar of the OR table to a position caudal to the "W" connection bar. For tiny newborns and premature infants, underlapping the positioning of the base station 70 relative to the rostral end of the OR tabletop 20 allows the infant's body to be physically supported by the OR table, while the head remains centered on the universal headrest 10 or the center point thereof. The center point "T" on FIGS. 7, 18, 19A, 19B, and 19C represents points on the concentric center axes of both arcuate rails 106, 110 depicted in the respective figures. As discussed previously, the brain retractors supported by various selectively moveable clamps 72 on the arcuate rails 106, 110 of base station 70 allow the surgeon to move retractors along orbital paths with the surgical target being approximately at or near the center of these orbital excursions, thereby simplifying the adjustment and repositioning of brain retractors. Furthermore, having the infant's body on the OR table provides physical support of the baby and facilitates keeping the baby warm.

Referring again to FIG. 19A through FIG. 19C, in embodiments with two arcuate rail members, the arcuate rail members are concentric with the center T. Further, in some implementations, the arcuate rail members have different radii, with as shown in FIG. 19B and FIG. 19C, one radius is greater than the other. As shown in FIG. 19A through FIG. 19C, in some embodiments, the horizontal support member passes proximate to the center T or may be offset from the center T by a distance to accommodate a surgical head holder. It should be appreciated, however, that in other embodiments, depending on the design of the surgical head holder, the horizontal support member may pass through the center.

Further, two of the three base station devices (FIG. 19B and FIG. 19C) have two arcuate rails on which one or more selectively moveable clamps 72 may be placed to support retractor arms, image guidance, and/or a surgical armrest which can be moved around the axis of the center point T of each of the respective base stations. Indeed, it is suggested that surgeons who do microneurosurgery intuitively position their patients in a surgical headrest attached to the OR table so that the surgical field, the operative target, and the actual surgical approach can all be readily and adequately visualized with the operating microscope. Moreover, a microsurgeon operating on an adult would likely not undertake surgery if the head position were not rigidly fixed. Accordingly, these three base station embodiments of FIGS. 19A, 19B, and 19C not only provide pin stabilization of the skull utilizing the surgical head holder 14 with multiple low-pressure pins, but also allow efficient and reliable positioning and repositioning of brain retractors and/or a surgical armrest.

Now referring to FIG. 19A through FIG. 26, it is apparent that the center-point base station 300 increases the arcuate limits of both the upper and lower rails. Like the single rail base station 302 and the double rail base station 304, the center-point base station 300 attaches to the OR table 12, utilizing the horizontal support member which receives the two horizontal rods that adjustably attach to the cross bar 24. The cross bar 24 also supports two fixed vertical rods 28, 30, which adjustably connect to respective bottom blocks 32, 34 of the center-point base station 300.

Figure 2:
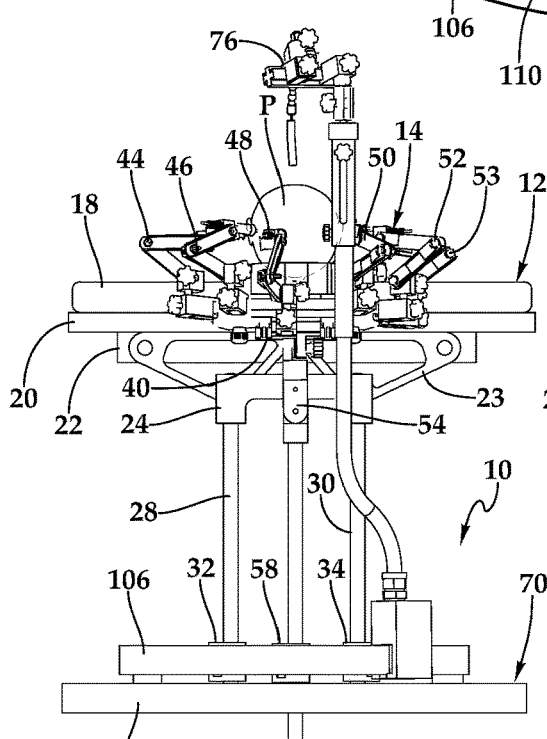
FIG. 2 is a cephalic elevation view of one embodiment of the operating room table, which is undraped, with the surgical head holder and the base station assembly to facilitate the use of various surgical accessories during the surgical procedure on a patient, according to the teachings presented herein.
Figure 3:
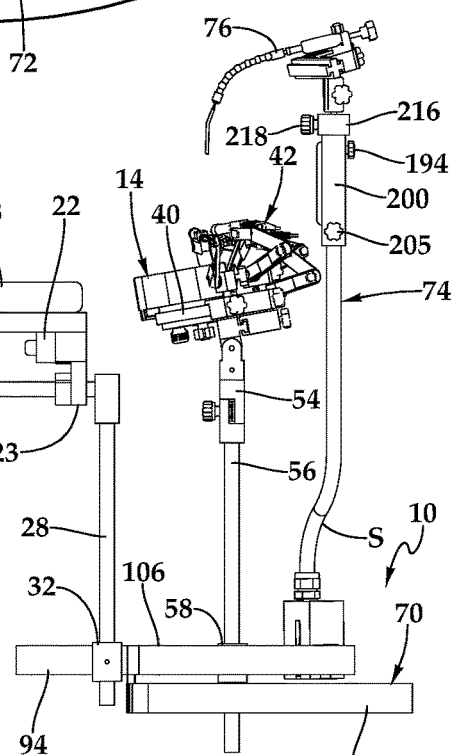
FIG. 3 is a lateral elevation view of the cephalic end of the operating room table with the base station assembly depicted in FIG. 2, without the patient.
Figure 4:
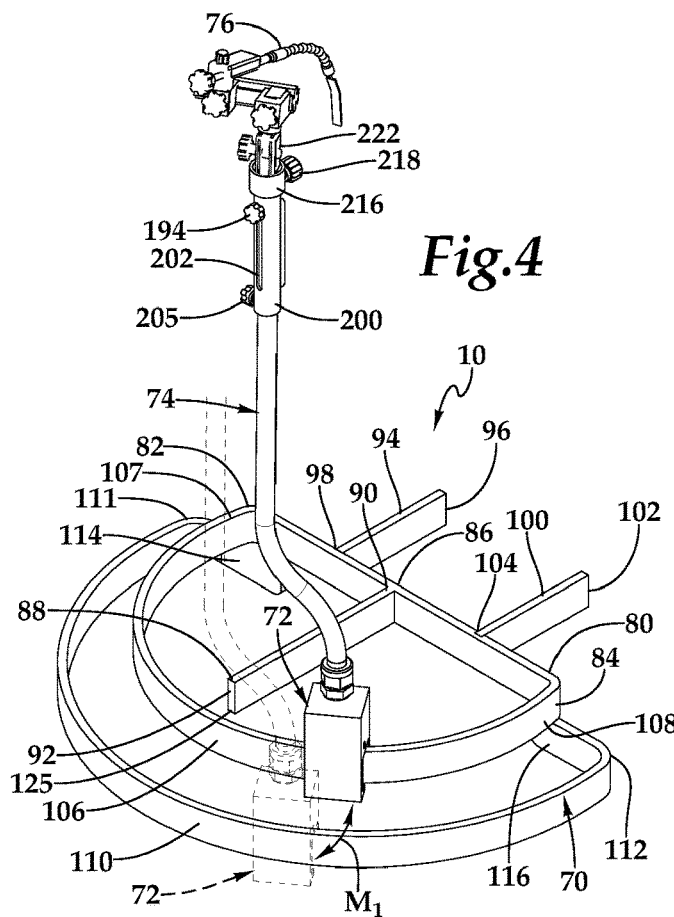
FIG. 4 is a cephalic dorsal perspective view of the base station assembly depicted in FIG. 2 without the patient, the surgical headrest, and the instrumentation to support the headrest.
Figure 5:
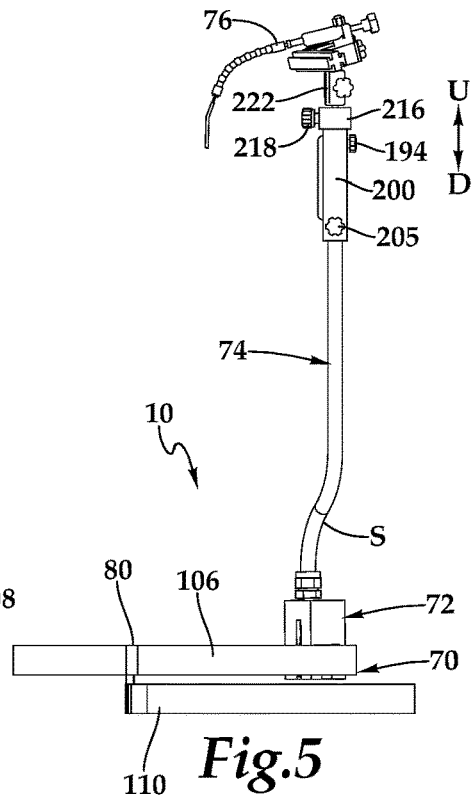
FIG. 5 is a lateral elevation view of the base station assembly depicted in FIG. 2, without the patient, the surgical head holder, nor the instrumentation to support the headrest.
Figure 6:
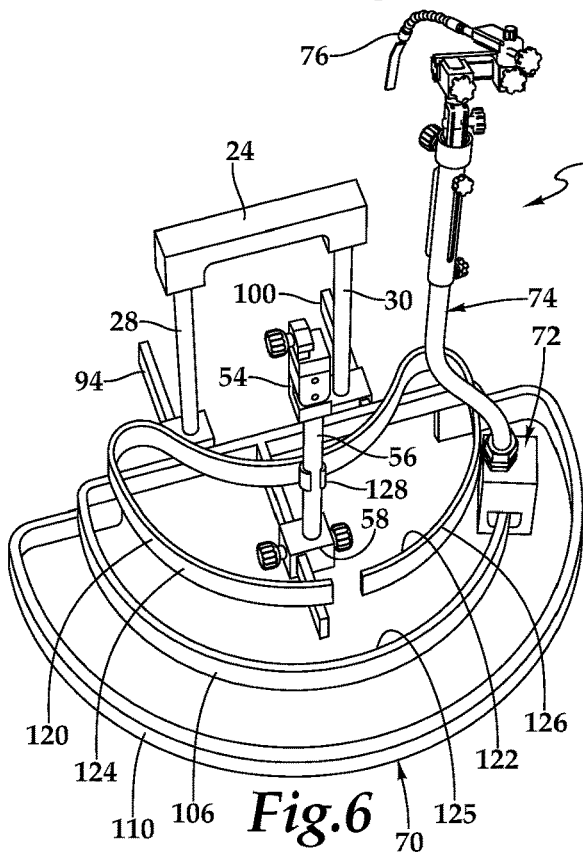
FIG. 6 is a cephalic dorsal perspective view of the base station assembly with a selectively moveable brain retractor as depicted in FIGS. 4 and 5, without the surgical head holder, the patient, and the OR table.
Figure 21:
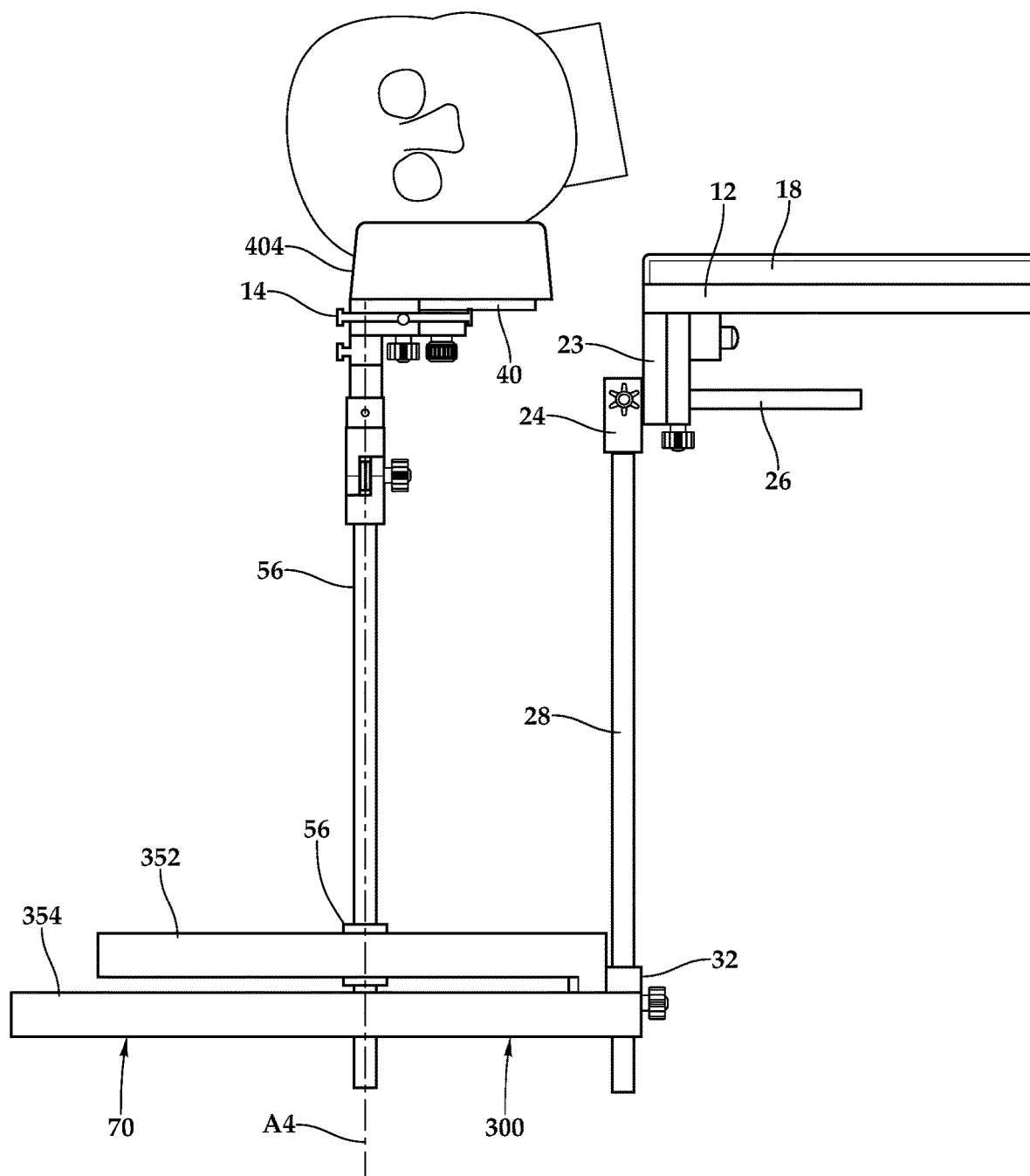
FIG. 21 is a lateral elevation view of an adult patient as depicted in FIG. 20, wherein the cross bar (shown with the six-star knob) is proximate the table connecting device.
Figure 26:
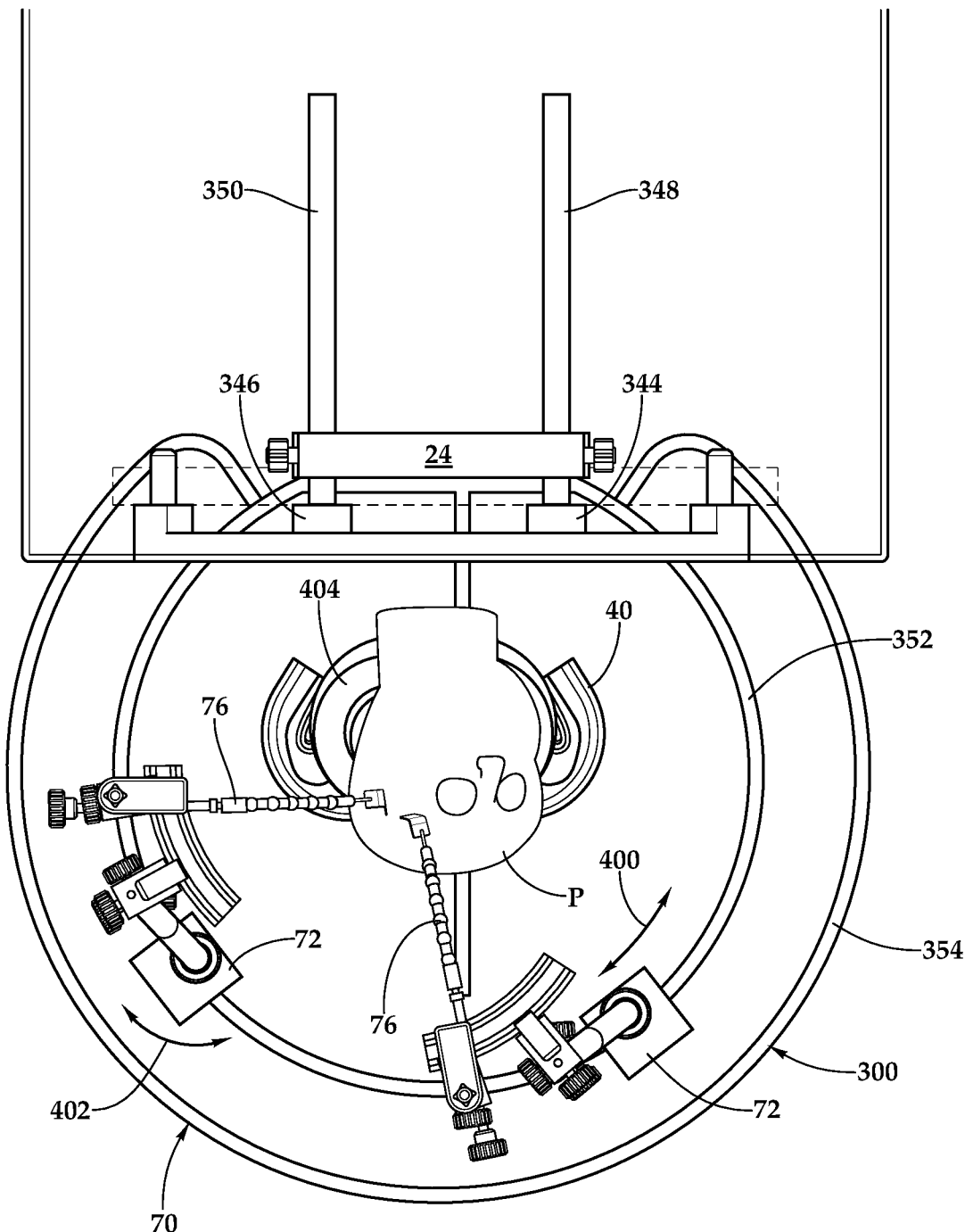
FIG. 26 is a top plan view of the center-point base station supporting the four (4)-month-old child in an oblique supine position for a left pterional operation with two selectively moveable clamps on the upper arcuate rail for supporting two (2) brain retractors, one on the temporal lobe and one the frontal lobe, respectively, with the retractors, (blades not shown for clarity) being readjusted as often as required by the complexities of the surgical procedure with or without the surgeon easily making changes in the positions of the selectively moveable clamps, thereby not requiring the circulating staff of the operating room to reach under wet and bloodied drapes to participate in the repositioning process.

With reference to FIG. 2, FIG. 3, and FIG. 19C, using the center-point base station 300 for patients ranging from children to adults, the cross bar 24 is positioned rostral to the horizontal support member 22 of the OR table 12 and the "W" table brace 23, best seen in FIG. 2. Such a design provides a maximal arcuate excursion of, by way of example, 286° of mobility for the selectively moveable clamp 72 on the upper arcuate rail 352 and, by way of example, a 274° excursion on the lower arcuate rail 354, as summarized in FIG. 20, with the mobility illustrated by arrows 400, 402. As shown, the selectively moveable clamp 72 is appropriately positionable and repositionable about the patient P resting on gel pads 404 of the headrest 40. FIG. 21 shows a lateral view of this adult-sized patient positioned on the surgical head holder 14 supported by the center-point base station configuration 300 of the base station 70. Pins and other components have been omitted for clarity. However, the setup of the center-point base station 300 for a small infant (4-months-old, for example) or a premature baby [thirty-five (35)-weeks gestational age, as another example] are illustrated in FIGS. 22 and 23 and FIGS. 24 and 25, respectively. For these small patients, the cross bar 24 is positioned caudal to the "W" table brace 23 so that the shoulders and torsos of these very small children are supported by the top of the OR table. In essence, moving the cross bar 24 behind the "W" table brace 23 of OR table 12 relocates the entire center-point base station 300 caudally, causing the caudal-most end of the center-point base station 300 to rest beneath the cephalic end of the OR table 12. Accordingly, the maximal arcuate excursions of the selectively moveable clamps 72 are reduced on both arcuate rails 352, 354, when used for these smallest children, but the versatility and efficiency of positioning and repositioning of brain retractors and/or a surgical armrest are entirely preserved. For instance, the maximal arcuate excursions of the selectively moveable clamp 72 on the arcuate rails 352, 354 are diminished by this maneuver to, by way of example, 260° on the arcuate rail 352 and, by way of example, 237° on the arcuate rail 354 for the four (4)-month-old infant. For the thirty-five (35)-week gestational age premature infant, the maximal arcuate excursions of the moveable clamp 72 on arcuate rails 352, 354 are, by way of example and not by way of limitation, 244° and 228°, respectively. As best shown in FIG. 26, in any of these embodiments in FIG. 20 through 25, various instruments may be appropriately placed and utilized with great mobility as shown by the arrows 400, 402.

In some operational implementations, the base station assembly 10 supports various surgical accessories, such as the surgical accessory 76, during a surgical procedure, such as an operation on the skull and brain. The base station 70 can accept either or both of two large orbital arcuate rails 106, 110 of base station 70 may receive one or more selectively moveable clamps 72 to be adjustably positioned by actuation of the control knobs 194 within the slot(s) 202 of the cylindrical sheaths 200 on the vertical support arm 74. Additionally, the height of a vertical support arm 74 may be adjusted as required using the control knob 205. Furthermore, a vertical support arm 74 can be selectively rotated and/or tilted slightly at its connection to end cap 160 on the dorsal surface of the selectively moveable clamp 72. This versatility in positioning mitigates spatial restrictions while providing enhanced surgeon control without the required assistance of others who are not scrubbed and without increased risk of contamination of the surgical field.

The use of the base station assembly 10 as part or component of a larger surgical system will now be discussed. With reference to FIG. 1 through FIG. 9, during some operational embodiments, the vertical support arm 74 is attached at an inferior end 174 to the selectively moveable clamp 72, as well as a superior end 172 to the cylinder sheath 200 along with the respective knobs 194, 205. The resulting assembly can thereby be sterilized as an assembled unit prior to surgery and be ready to be handed to the scrub technician by a circulating operating room nurse, according to standard operating room protocol. When the surgeon wishes to attach the selectively moveable clamp 72 to one of the arcuate rail members 106, 110, he or she simply holds the entire assembly, comprised of the cylindrical sheath 200, the vertical support arm 74, and the selectively moveable clamp 72 at its upper end, grasping the cylindrical sheath 200, thereby suspending the selectively moveable clamp 72 such that it hovers over the intended appropriate arcuate rail member 106, 110. It should be noted that arcuate rail member 106, 110 would be approximately at knee level and would therefore not be considered sterile. As discussed herein, the selectively moveable clamp 72 may be moved between the arcuate rail member 106 and the arcuate rail member 110, if and when it were required, as shown by arrow $M_1$. The circulating operating room nurse may then take hold of the selectively moveable clamp 72 at the body 130, guiding the body 130 so that the arcuate rail member 106 or arcuate rail member 110 is accepted into the distance d formed between the rollers 140, 144 and the rollers 142, 146.

Moreover, with some practice, the surgeon will likely be able to connect the selectively moveable clamp 72 attached to the vertical support arm 74 and the cylindrical sheath 200 to the base station 70 without any external help. Accordingly, with the control knob 194 in the release position, the surgeon can move the entire selectively moveable clamp 72 with the vertical support arm 74 around the base station 70 attached to the operating room table 12 by moving the top of the cylindrical sheath 200. Standard operating room protocol considers surgical drapes to be sterile above a horizontal plane that approximates the bottom edge of the operating room tabletop 14, below which surgical sterility is assumed questionable. Scrubbed operating room personnel are taught that they are considered sterile down to their waist, but not below. Similarly, the base station assembly 10 should be considered sterile down to this same approximate level, and the surgical team must avoid contaminating themselves by touching the lower part of the base station assembly 10. Indeed, the lower half of the vertical support arm 74 may have a different color or a distinctive brushed or ribbed finish as a reminder that this area is not considered sterile. This should not present any problem, however, since the operating room team should already know that one cannot lower his or her arms below the waist.

It is suggested that the bottoms of the surgical drape 36 that fall naturally from the draping of the head of the patient P be gathered with sterile gloves by a circulating operating room nurse and tucked inside the inner rail member 110 of the two rail, vertically offset embodiment. If the surgeon is utilizing a single rail embodiment, the drapes should be positioned within the single rail, whether it be rail member 106 or 110. As mentioned, if the surgeon has the OR table set to be very high, the bottoms of the drapes may be higher than any of the rails, regardless of which embodiment is being utilized, and the drape holder 120 will be required to control the drapes within the arcuate space 122 defined by the drape holder 120. In this way, both arcuate rail members 106, 110 may be easily seen by the surgeon, and the selectively moveable clamps 72 and their respective vertical support arms 74 can be attached and moved about their respective arcuate rail members 106, 110 as the surgeon so desires from the start of surgery and throughout the operative procedure. Obviously, the surgeon may prefer to use the drape holder 120 for all occasions, because it ensures the best visualization of the arcuate rails 106, 110, which may facilitate the placement of various selectively moveable clamps 72 on the base station 70. If the surgeon requires the height of the operating room table 12 to be unusually high, the tails of the surgical drape 36 may end above the height of the arcuate rail member 106, which would normally hold the surgical drape 36 out of the way, as discussed previously. In this case, the drape holder 120 can simply be adjustably moved toward the top of the OR table as necessary.

Once the surgeon has attached the selectively moveable clamp 72 to the base station 70, the surgeon can make positioning adjustments then or at any subsequent time during surgery without external help. This feature provides remarkable adjustability of surgical accessories such as brain retractors and surgical armrests all controlled by the surgeon without requiring assistance from the circulating operating room nursing staff. Simply loosening the control knob 194 on the vertical support arm 74 allows the surgeon to move an accessory such as a brain retractor(s) around the 286° or 274° arcuate pathways of the rails 106, 110 of the center-point base station 300, for example, as required during surgery, and repositioning can be repeated whenever necessary. This remarkable adjustability of positioning of the selectively moveable clamps 72 is illustrated in FIG. 20. On the other hand, a selectively moveable clamp 72 can be added to or removed from an arcuate rail 106, 110 at any time. Moreover, the surgeon can rotate the elongated member 170 at its attachment to the selectively moveable clamp 72 at the joint 162, thereby moving an accessory closer or farther away from the operative site because of the curve S configuration of the elongated member 170. It may be necessary to adjust the radial positioning of the selectively moveable clamp 72 on the base station 70 as part of this maneuver. If desired by the surgeon, the elongated member 170 will tilt slightly on its attachment at joint 162 for more subtle adjustment which can be maintained by tightening the control knob 194 to lock the selectively moveable clamp 72 and its relationship to the elongated member 170 in position. With respect to FIGS. 7A and 7B, there may be space around the joint 162, by way of machining or other technique, to allow some "play" when tightening occurs. Approximately 7° of tilt at the joint 162 can be so achieved, which correspondingly moves the ring member 216 at the top of the vertical support arm 74 approximately 3 cm in a plane parallel to the floor. It is therefore suggested that tilting of the vertical support arm 74 is a quick and simple method to achieve subtle positioning adjustment of the accessory 76.

As mentioned, at the superior end 172 of the elongated member 170, the attachment member 198 may include the cylindrical sheath 200 with the hand adjustment knob 218 to adjust the height of the cylindrical sheath 200, which can telescope on the vertical support arm 74 and be locked in place with the hand adjustment knob 205. Indeed, the lengths (the height, functionally speaking) of the vertical support arm 74 may be whatever is comfortable for the operating team, and embodiments of different lengths can be kept sterile to address surgeon preference.

Moreover, various selectively moveable clamps 72 with vertical support arms 74 can be added to or removed from the base station 70 as needed without having to struggle with wet, bloody drapes. After an anesthetized patient is positioned on the headrest 40 and the surgical site is prepped and draped, the surgical drapes are gathered together within the base station 70, such as within the drape holder 120, or alternatively, within the arcuate rail member 106 or the arcuate rail member 110 in a base station 70 configured with only the outer arcuate rail member, as mentioned previously. In this way, the 210° and 195° orbits, for example, of the double rail base station 302 remain freely accessible initially and throughout the surgical procedure. The surgeon determines how many selectively moveable clamps 72 may be needed for the procedure. The various vertical support arms 74 may be positioned where the surgeon thinks they will be required, or they may be clustered at either or both arcuate ends of the base station 70 to be moved into place later as needed. Additional selectively moveable clamps 72 with vertical support arms 74 may be added or removed as needed at any time during the surgery. As mentioned, it should be appreciated that the traffic involving the selectively moveable clamps 72 may require forethought and planning. Using two arcuate rail members allows one selectively moveable clamp 72 to be moved past another selectively moveable clamp 72 without interrupting the process of surgery.

The order of execution or performance of the methods and process flows illustrated and described herein is not essential, unless otherwise specified. That is, elements of the methods and process flows may be performed in any order, unless otherwise specified, and that the methods may include elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A base station assembly for an operating room table, the base station assembly comprising:
   a base station having a selectively moveable clamp attached thereto;
   the selectively moveable clamp having a vertical support arm extending therefrom; and
   the selectively moveable clamp including:
      a body having an upper end and a lower end, the body including a first rail frame and a second rail frame, a distance between the first rail frame and the second rail frame set to accommodate a width of a rail of the base station;
      a first roller secured to the first rail frame, the first roller configured to be placed on the rail;
      a second roller secured to the second rail frame, the second roller configured to be placed on the rail;
      a finger lock coupled to the body for pivoting movement in a mandibular motion relative to the first rail frame, the finger lock configured to be placed in a braking relationship with the rail;
      a receiving member intersecting the body at the upper end, the receiving member retaining a clamp pin, the clamp pin located suprajacent the finger lock with axial movement, the clamp pin configured to actuate the finger lock between an open position and a closed position;
      in the open position, the clamp pin being disengaged with the finger lock;
      in the closed position, the clamp pin being engaged with the finger lock to force the finger lock into the braking relationship with the rail;
   wherein the vertical support arm comprises an elongated member having a channel extending from a proximal end to a distal end, a ball-bearing train disposed within the channel, and a drive member at the proximal end configured to urge the ball-bearing train axially within the channel so as to advance the clamp pin from the open position to the closed position, thereby forcing the finger lock into the braking relationship with the rail.

2. The base station assembly as recited in claim 1, wherein the finger lock in the braking relationship with the rail inhibits movement along the rail in the closed position.

3. The base station assembly as recited in claim 1, wherein the first rail frame and the second rail frame define a chamber and the finger lock is coupled to the body for pivoting movement by a pivot pin which extends from the body into the chamber.

4. The base station assembly as recited in claim 1, wherein the clamp pin extends into the chamber to engage the finger lock in the closed position.

5. The base station assembly as recited in claim 1, wherein, in the open position, the first roller and the second roller facilitate movement of the selectively moveable clamp along the rail.

6. The base station assembly as recited in claim 1, wherein the first roller and the second roller, in combination, further comprise a shape for accommodating the rail with the rail having an arcuate form.

7. The base station assembly as recited in claim 1, wherein the first roller and the second roller, in combination further comprise a shape for accommodating the rail with the rail having a rectangular form.

8. The base station assembly as recited in claim 1, wherein the upper end of the body supports the vertical support arm.

9. A base station assembly for an operating room table, the base station assembly comprising:
   a base station having an arcuate rail thereon;
   a selectively moveable clamp attached to the arcuate rail of the base station, the selectively moveable clamp having a body with an upper end and a lower end, the body including a first rail frame and a second rail frame defining a chamber therebetween, and a first roller and a second roller disposed respectively on the first rail frame and the second rail frame for movement along the arcuate rail;

a finger lock pivotally coupled to the body by a pivot pin extending into the chamber, the finger lock configured to pivot in a mandibular motion between an open position and a closed position in which the finger lock frictionally engages the arcuate rail to inhibit movement of the selectively moveable clamp; and a vertical support arm extending from the upper end of the body, the vertical support arm including:

an elongated member having a channel extending from a first end adjacent the upper end of the body to a second end spaced apart from the body, a ball-bearing train disposed within the channel, a clamp pin disposed proximate the second end of the elongated member and aligned to contact the finger lock in the closed position, and a drive member disposed proximate the first end of the elongated member and operably coupled to the ball-bearing train, wherein rotation of the drive member in a first direction advances the ball-bearing train axially within the channel to urge the clamp pin against the finger lock and pivot the finger lock from the open position to the closed position, and rotation of the drive member in a second direction retracts the ball-bearing train within the channel to release the clamp pin from the finger lock and permit movement of the selectively moveable clamp along the arcuate rail.

10. A base station assembly for an operating room table, the assembly comprising:

a base station having a rail thereon;

a selectively moveable clamp disposed on the rail, the clamp including:

a body with an upper end and a lower end, the body including a first rail frame and a second rail frame spaced apart to define a clearance for the rail;

a first roller and a second roller each associated with the body and configured for movement along the rail;

a finger lock pivotably coupled to the body about a pivot pin, the finger lock movable in a jaw-like mandibular motion between an open position and a closed position in which the finger lock frictionally engages the rail to inhibit movement of the clamp; and a vertical support arm extending from the upper end of the body, the vertical support arm comprising:

an elongated member having a channel extending between a proximal end and a distal end;

a ball-bearing train disposed within the channel;

a clamp pin disposed near the distal end of the elongated member and aligned to contact the finger lock in the closed position; and a drive member located at the proximal end of the elongated member and operably coupled to the ball-bearing train, such that rotation of the drive member in a first direction advances the ball-bearing train axially to urge the clamp pin against the finger lock and pivot the finger lock into the closed position, and rotation of the drive member in a second direction retracts the ball-bearing train to release the clamp pin from the finger lock and permit movement of the selectively moveable clamp along the rail.

* * * * *